(12) United States Patent
    Brand

(10) Patent No.: US 10,213,382 B2
(45) Date of Patent: Feb. 26, 2019

(54) NANOSUSPENSION OF NATURAL MATERIALS AND PREPARATION METHOD THEREOF

(71) Applicant: APURANO PHARMACEUTICALS GMBH, Munich (DE)

(72) Inventor: Werner Brand, Munich (DE)

(73) Assignee: APURANO PHARMACEUTICALS GMBH, Munich (DE)

( * ) Notice: Subject to any disclaimer, the term of this patent is extended or adjusted under 35 U.S.C. 154(b) by 0 days.

(21) Appl. No.: 15/116,434

(22) PCT Filed: Feb. 3, 2015

(86) PCT No.: PCT/EP2015/052202
    § 371 (c)(1),
    (2) Date: Aug. 3, 2016

(87) PCT Pub. No.: WO2015/114164
    PCT Pub. Date: Aug. 6, 2015

(65) Prior Publication Data
    US 2016/0346201 A1    Dec. 1, 2016

(30) Foreign Application Priority Data

Feb. 3, 2014   (EP) .................................... 14153705
Jul. 7, 2014   (EP) ................... PCT/EP2014/064449

(51) Int. Cl.
    *A61K 9/10*    (2006.01)
    *A61K 31/716*  (2006.01)
    (Continued)

(52) U.S. Cl.
    CPC .................. *A61K 9/10* (2013.01); *A61K 9/14* (2013.01); *A61K 9/145* (2013.01); *A61K 31/716* (2013.01);
    (Continued)

(58) Field of Classification Search
    None
    See application file for complete search history.

(56) References Cited

U.S. PATENT DOCUMENTS

| 4,648,719 A | 3/1987 | Röben |
| 8,338,564 B2 | 12/2012 | Wong |

(Continued)

FOREIGN PATENT DOCUMENTS

| CA | 2082562 A1 | 5/1993 |
| CN | 1 416 847 A | 5/2003 |

(Continued)

OTHER PUBLICATIONS

CN1757601 EPO translation, last visit date: Jun. 19, 2017.*

(Continued)

*Primary Examiner* — Ernst V Arnold
*Assistant Examiner* — Kyung S Chang
(74) *Attorney, Agent, or Firm* — Grüneberg and Myers PLLC

(57) ABSTRACT

The present disclosure relates to a method for the preparation of a nanosuspension of at least one natural material, wherein the method comprises the steps of (a) providing at least one natural material having a particle size ($D_{90}$) of less than 320 μm; (b) dispersing said at least one natural material of step (a) in a solvent; and (c) milling the dispersion of step (b) to a particle size ($D_{90}$) of below 1000 nm. The nanosuspension is useful for the preparation of a medicament.

20 Claims, 11 Drawing Sheets

(51) Int. Cl.
  *A61K 36/63* (2006.01)
  *A61K 9/14* (2006.01)
  *A61K 35/748* (2015.01)
  *A61K 36/07* (2006.01)
(52) U.S. Cl.
  CPC ............ *A61K 35/748* (2013.01); *A61K 36/07* (2013.01); *A61K 36/63* (2013.01)

(56) References Cited

U.S. PATENT DOCUMENTS

| | | | |
|---|---|---|---|
| 2001/0016467 A1* | 8/2001 | Weichert | B02C 17/14 451/32 |
| 2003/0060404 A1 | 3/2003 | Heinz et al. | |
| 2004/0033202 A1* | 2/2004 | Cooper | A61K 9/145 424/46 |
| 2004/0249138 A1 | 12/2004 | Lawson et al. | |
| 2006/0062926 A1* | 3/2006 | Richardson | A01N 59/20 427/440 |
| 2006/0233845 A1* | 10/2006 | Lukowski | A61K 9/1664 424/401 |
| 2008/0279928 A1* | 11/2008 | Moschwitzer | A61K 9/10 424/455 |
| 2010/0272980 A1 | 10/2010 | Kowata et al. | |
| 2011/0104358 A1 | 5/2011 | Furuta et al. | |
| 2011/0274908 A1 | 11/2011 | Kowata et al. | |
| 2012/0042886 A1* | 2/2012 | Piskorz | A61K 9/0073 131/273 |
| 2012/0156309 A1 | 6/2012 | Eckert et al. | |
| 2012/0244134 A1 | 9/2012 | Chen et al. | |
| 2013/0209651 A1 | 8/2013 | Furuta et al. | |
| 2015/0283070 A1* | 10/2015 | Stenzler | A61K 9/0075 424/489 |

FOREIGN PATENT DOCUMENTS

| | | |
|---|---|---|
| CN | 1757601 A * | 4/2006 |
| EA | 200701793 A1 | 2/2008 |
| EP | 0 188 737 A2 | 7/1986 |
| EP | 1 389 466 A1 | 2/2004 |
| EP | 2 226 171 A1 | 9/2010 |
| EP | 2 266 415 A1 | 12/2010 |
| EP | 2 581 092 A1 | 4/2013 |
| JP | 5-221852 A | 8/1993 |
| JP | 5-262659 A | 10/1993 |
| JP | 2005-97308 A | 4/2005 |
| JP | 2009-155384 | 7/2007 |
| JP | 2009-263638 A | 11/2009 |
| JP | 2010-83839 A | 4/2010 |
| KR | 20090057480 | 6/2009 |
| KR | 10-2010-0093080 | 8/2010 |
| RU | 2260445 C2 | 10/2003 |
| WO | WO 01/01963 A1 | 1/2001 |
| WO | 2002/024163 | 3/2002 |
| WO | WO 03/045167 A1 | 6/2003 |
| WO | WO 2006/091780 A2 | 8/2006 |
| WO | WO 2011/155518 A1 | 12/2011 |
| WO | 2013/168437 | 11/2013 |

OTHER PUBLICATIONS

Reducol™ plant phytosterol powder brochure ([retrieved from on-line website: http://reducol.com/what-is-reducol/, last visit Jun. 24, 2017]).*

International Search Report dated Apr. 7, 2015 in PCT/EP2015/052202 filed Feb. 3, 2015.

S. Kobierski et al, *Pharmazie*, "resveratrol nanosuspensions for dermal application—production, characterization, and physical stability", 64: 741-747 (2009).

"Forbes Medi-Tech Receives US Patent"—Reducol™ plant phytosterol powder brochure, 2016, Pharmachem Laboratories. Inc. ([retrieved from on-line website: http://reducol.com/forbes-medi-tech-receives-us-patent/ last visit Nov. 6, 2017).

"Plurol Oleique" National Center for Biotechnology Information, U.S. National Library of Medicine ([retrieved from on-line website: https://pubchem.ncbi.nlm.nih.gov/compound/9963243 last visit May 29, 2017).

"Gelucire® 44/14: Lauroyl polyoxyl-32 glycerides NF from Gattefossé" American Pharmaceutical Review ([retrieved from on-line website: http://www.americanpharmaceuticalreview.com/25260-Excipients/9506442-Gelucire-44-14-Lauroyl-polyoxyl-32-glycerides-NF/ last visit May 29, 2017).

"Labrafil® M1944 CS: Oleoyl polyoxyl-6 glycerides NF from Gattefossé" American Pharmaceutical Review ([retrieved from on-line website: http://www.americanpharmaceuticalreview.com/25260-Excipients/9506443-Labrafil-M1944-CS-Oleoyl-polyoxyl-6-glycerides-NF/ last visit May 29, 2017).

"Labrasol® Caprylocaproyl polyoxyl-8 glycerides NF from Gattefessé" American Pharmaceutical Review ([retrieved from on-line website: http://www.americanpharmaceuticalreview.com/25260-Excipients/7682699-Labrasol/ last visit May 29, 2017).

Decision of Rejection in Japanese Patent Appiication No. 2016-567161, dated Feb. 6, 2018 (with English language translation).

* cited by examiner

NANOSUSPENSION OF NATURAL MATERIALS AND PREPARATION METHOD THEREOF

CROSS REFERENCE TO RELATED APPLICATION

This application is a National Stage entry under 35 USC 371 of PCT/EP2015/052202, filed on Feb. 3, 2015, and claims priority to European Patent Application No. 14153705.0, filed on Feb. 3, 2014 and PCT/EP2014/064449, filed on Jul. 7, 2014.

BACKGROUND OF THE INVENTION

Field of the Invention

The present application relates to a method for the preparation of a nanosuspension from natural materials, to a nanosuspension comprising at least one natural material, and the use of such nanosuspension for the preparation of a medicament.

Background of the Invention

Natural materials, such as plants, cyanobacteria, algae or fungi, contain active agents which have the potency for treating diseases. In order to elute these active agents from natural materials, a variety of pharmaceutical preparations are known including aqueous or alcoholic percolation or maceration, dried powder extracts in form of tablets or capsules, or injectable dosage formulations. However, there are many disadvantages associated with these types of administration. Many of the ingredients are degraded within the gastrointestinal tract or undergo first-pass metabolism in the liver. In addition, parts of the population experience difficulty swallowing pills or are unable to tolerate any solids. Furthermore, many active agents of natural materials are poorly water soluble. The potency and therapeutic effects of many active agents of natural materials are therefore limited.

U.S. Pat. No. 5,858,410 relates to drug preparations called "nano-suspensions" which are produced by high-pressure homogenization. Prior to the use of high pressure homogenization, nano-suspensions were prepared by a pearl milling process, which is a time consuming process compared to pressure homogenization. This technology is the subject of, inter alia, U.S. Pat. No. 5,271,944. A number of other methods have been used to prepare nano-suspensions with various degrees of success including low energy agitators, turbine agitators, colloid mills, sonolators, orifices, media mills, rotor stator mixers and sonicators.

Chinese patent application No. CN 1 416 847 A relates to a preparation of a nanosuspension of *Radix Panacis Quinquefolii* (American *ginseng*) produced by high-pressure homogenization at a concentration of between 20% and 11.1% (w/w).

European patent publication No. EP 2 226 171 A1 relates to a disintegration of wooden material (e.g. Douglas fir) by a millstone type grinder to provide cellulose fibers having an average fiber diameter of at most 30 nm and a corresponding cellulose fiber composite made thereof. The fibers have an average minimum length of 50 μm.

However, the prior art methods for preparing a nano-suspension lack a method for the preparation of a nano-suspension from natural materials with a high amount of natural material, i.e., a high concentration of natural material. There is thus still a need for methods for preparing a nano-suspension from natural materials, which nano-suspension may be advantageously used in the treatment or prevention of diseases.

SUMMARY OF THE INVENTION

It is thus one object of the present disclosure to provide a method for the preparation of a nanosuspension from the whole or parts of natural materials which may be used in the preparation of a medicament.

In a first aspect, the present disclosure provides a method for the preparation of a nanosuspension as disclosed in claim 1.

In another aspect, the present disclosure provides a nanosuspension obtainable according to a method of the first aspect.

In another aspect, the present disclosure provides a nanosuspension according to the first aspect for use in the preparation of a medicament for buccal, topical or oral application to an animal, preferably a human, or for use in the preparation of a medicament for parenteral, intrathecal, intravenous, transdermal, or trans-mucosal application, preferably buccal, topical or oral application, to an animal, preferably a human.

In another aspect, the present disclosure provides a nanosuspension according the first aspect for use in the treatment or prevention of cancer, inflammatory bowel disease (IBD), arthritis, human immunodeficiency virus (HIV), other viral diseases, dermatological diseases, such as neurodermatitis or psoriasis, or auto-immune diseases, such as multiple sclerosis.

In still another aspect, the present disclosure provides the use of a nanosuspension according to the first aspect for the preparation of a medicament.

In still another aspect, the present disclosure provides a method for the treatment or prevention of cancer, inflammatory bowel disease (IBD), arthritis, human immunodeficiency virus (HIV), other viral diseases, dermatological diseases, such as neurodermatitis or psoriasis, or auto-immune diseases, such as multiple sclerosis comprising administering an effective amount of a nanosuspension according to the first aspect to a patient in need thereof.

DETAILED DESCRIPTION OF THE INVENTION

Figure 1:
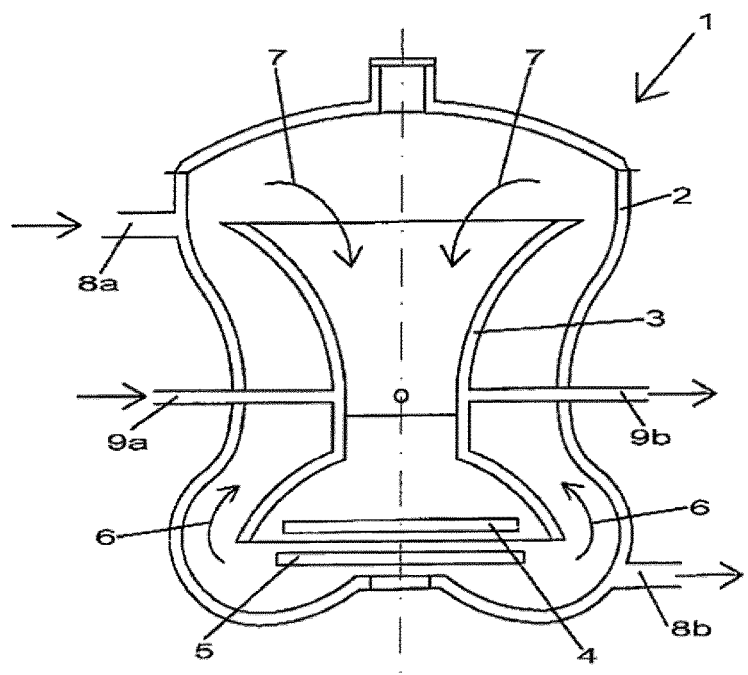
FIG. 1 shows the schematic drawing of a colloidator.

The present disclosure relates to a method for the preparation of a nanosuspension comprising at least one natural material, wherein the method comprises the steps of
  a. Providing at least one natural material having a particle size ($D_{100}$) of less than 320 μm;
  b. Dispersing said at least one natural material of step a. in a solvent;
  c. Milling the dispersion of step b. to a particle size ($D_{90}$) of below 1000 nm ($D_{90}$<1000 nm).

The present invention as illustratively described in the following may suitably be practiced in the absence of any element or elements, limitation or limitations not specifically disclosed herein.

The present invention will be described with respect to particular embodiments and with reference to certain figures but the invention is not limited thereto but only by the claims. Terms as set forth hereinafter are generally to be understood in their common sense unless indicated otherwise.

Where the term "comprising" is used in the present description and claims, it does not exclude other elements. For the purposes of the present invention, the term "consisting of" is considered to be a preferred embodiment of the term "comprising". If hereinafter a group is defined to comprise at least a certain number of embodiments, this is also to be understood to disclose a group, which preferably consists only of these embodiments.

Where an indefinite or definite article is used when referring to a singular noun, e.g. "a", "an" or "the", this includes a plural of that noun unless something else is specifically stated.

Terms like "obtainable" or "definable" and "obtained" or "defined" are used interchangeably. This, e.g., means that, unless the context clearly dictates otherwise, the term "obtained" does not mean to indicate that e.g. an embodiment must be obtained by e.g. the sequence of steps following the term "obtained" even though such a limited understanding is always included by the terms "obtained" or "defined" as a preferred embodiment.

A "nanosuspension" as used herein refers to a suspension of nano-particles in a solvent, such as, for example, water, ethanol, or a mixture thereof. The nanosuspension may additionally comprise stabilizing agents, or other compounds. A nanosuspension comprises a poorly water-soluble compound in the form of nano-particles suspended in a solvent. Such nanosuspension is used to enhance the "solubility" (or dispersibility) of a compound that is poorly soluble in a solvent, a lipid media, or both. As a result of increased "solubility", a higher plasma blood level of the poorly soluble compound is reached and the maximum plasma blood level of said compound is reached faster. The terms "suspension" and "dispersion" are used interchangeably in the present disclosure, as they refer to solid particles in a solvent.

"Nano-particles" as used herein are particles having a particle size of below 1000 nm. The compound nano-particles in the solvent may be primary particles, or agglomerated particles composed of smaller particles. The particle size in the nanosuspension may be measured with a laser diffraction analyzer (e.g. Beckman Coulter LS 13320 or Horiba LA-950).

The term "solubility" or "solubility limit" of a natural material as used in the present disclosure relates to the maximum amount of natural material that may be dissolved in a solvent. For the purposes of the present disclosure, the solubility of a natural material in a specific solvent may be determined as follows: an initial amount of dry natural material with a particle size $D_{90}$<320 μm is used to prepare a suspension of said natural material in a solvent, such as distilled water, at a concentration of 5% or 10% (w/w). For the preparation of said suspension, the natural material is suspended for 60 minutes in a solvent at a temperature of 30° C. The resulting suspension is then centrifuged at 1500 g for 30 minutes, and precipitates are separated from supernatant and weighed for control reasons. The supernatant is dried at 60° C. for 24 h, resulting in the natural material dissolved in the supernatant (dry basis), and weighed. The solubility is calculated using the following equation:

Solubility (%)=mass of supernatant (dry basis)×100/
mass of initial natural material powder (dry
basis).

The term "solubility factor" as used in the present disclosure relates to the amount of a natural material in a nanosuspension according to the present disclosure in relation to the solubility or solubility limit of said natural material in the solvent used to prepare the nanosuspension. The solubility factor is the amount of natural material present in the nanosuspension (in % (w/w)) divided by the solubility of said natural material in the solvent used. In other words, if a solubility factor of 1 is given, the solubility limit of the natural material in said solvent is reached. At a solubility factor below 1, the amount of natural material in the nanosuspension is below the solubility limit, and a solubility factor of above 1 indicates that more than the amount of natural material soluble in said solvent is present in the nanosuspension, i.e., the concentration of the natural material in the nanosuspension is above its solubility limit.

The term "cellulose fiber" as used in the present disclosure relates to a plant fiber (especially wood fiber) consisting of a polysaccharide with a linear chain of several hundred to over ten thousand β-1,4-D-glucose units with a length of the fiber of >1 μm. Cellulose fibers therefore do not consist of β-1,3/1,6-glucan with a geometrical shape of a sphere with a diameter <1 μm or an ellipsoid with semiaxis length <1 μm.

In a preferred embodiment, the at least one natural material is selected from the group consisting of plants, preferably plants excluding *ginseng* and/or cellulose fibers, cyanobacteria, algae and fungi. In another embodiment, the natural material does not comprise *ginseng* and/or cellulose fibers. The plants as used herein may comprise spermatophytina, which may comprise ginkopsida (gingko), gnetopsida, coniferopsida (e.g. needle trees) and angiosperms (flowering plants), which may further comprise the subclasses such as magnoliidae, liliidae (e.g. pineapple), malpighiales (e.g. St. John's wort, willow bark), rosidae (e.g. nettle), brassicales (e.g. *carica papaya*), fabales (e.g. *astragalus*), lamiales (e.g. olive tree and olive leaves), dispsacales (e.g. elder). Cyanobacteria may comprise e.g. spirulina. Algae may comprise the domains rhodobionta (e.g. red algae, brown algae and diatoms), green algae and glaucobionta. Fungi may comprise acrasobionta, myxomycota, heterokontobionta, and mycobionta (e.g. pillar fungi like *agaricus subrufescens*).

In another preferred embodiment the natural materials are gingko, pineapple, St. John's wort, willow bark, nettle, *carica papaya, astragalus*, olive leaves, elder, spirulina, *chlorella* algae, red algae, brown algae and diatoms green algae and glaucobionta, *agaricus subrufescens*, boswellia, rodiola *rosea*, chincona bark, ipecac, boneset, bryony anil, anil root, *curcuma*, devil's claw, cat's claw, *cystus incanus*, flax seed, *sylibum marianum* (holy thistle), *chelidonium majus* (celandine), kaplan-pelargonie, *echinacea*, grape seeds.

In another preferred embodiment, the natural material does not comprise *ginseng* and/or cellulose fibers.

In another preferred embodiment, the at least one natural material is a part or the whole of said natural material, preferably the whole of said natural material. The method of the present disclosure may be used for any natural material as a whole, or parts thereof. As an example, only parts of a plant may be used, such as the roots, stems, leaves, fruits, flowers, or the like, depending on the type of natural material.

In another preferred embodiment, the nanosuspension comprises a mixture of at least two natural materials. As such, the nanosuspension may be a nanosuspension containing a single natural material, or a mixture of more than one natural material, i.e., at least two natural materials.

The nanosuspension may as well comprise different parts of the same natural material, such as, e.g., parts of the root and parts of the flowers, and/or the nanosuspension may comprise different types of natural materials, such as, e.g., different plants or a plant and a cyanobacteria.

In another preferred embodiment, the natural material as used in the preparation of the nanosuspension is dried in a step a.1, prior to step a., preferably freeze-dried and/or thermally dried.

In another preferred embodiment, the natural material as used in the preparation of the nanosuspension and provided in step a. of the method as disclosed above has a water content w of below 15% (w<15%), preferably below 12% (w<12%), more preferably below 10% (w<10%), and most preferably below 8% (w<8%).

The water content of the natural material as used for the preparation of the nanosuspension preferably has a low water content. The term "water content" or "residual moisture" as used in the present disclosure refers to the water content w of the material, such as the natural material, calculated from the mass of the moist or wet material $m_{wet}$ and the mass of the dry material without water $m_{dry}$ and the mass of the material with a residual moisture $m_{res}$ by use of the following formula: residual moisture content [%] $w=(m_{res}-m_{dry})/(m_{wet}-m_{dry})*100\%$ Such low water content may be advantageous when preparing the nanosuspension. In addition, it may be helpful when bringing the natural material to a particle size ($D_{100}$) of less than 320 μm. There are different methods known in the art to reduce the water content of a natural material, and any of these methods may be used in combination with the present disclosure. As an example, the natural material may be lyophilized (i.e., freeze-dried) or thermally dried. It may be advantageous to clean, peal and/or core the natural materials, depending on the type of natural material prior to the drying step. In the following, two exemplary methods for drying are given.

Natural materials can be lyophilized with a lyophilizer, e.g., in a four-step process as follows:

- The natural material is cut into smaller pieces of about 1-2 cm with a knife depending on the size and structure of the natural material;
- The 1-2 cm pieces are put in a knife mill (e.g. Grindomix® 200 or 300 from Retsch GmbH, Germany) and ground with the following parameters: 10 sec at 2000 rpm following 10 sec at 5000 rpm and terminal 20 sec at 10.000 rpm;
- The resulting pulp is frozen at −18° C. for 4 h and further put into a lyophilizer and lyophilized until the product temperature is 20° C.

It is understood that the above freeze drying process is exemplary, and a person skilled in the art may adapt the process, depending on the type of the natural material. As an example, cyanobacteria may be directly freeze-dried, without prior grinding or cutting. Similarly, also the parameters for cutting the pieces in a knife mill may be adjusted according to the needs.

Natural materials can be also dried on air or in an oven at a temperature of, e.g., 36-45° C. until the residual moisture content is as low as 8%, depending on the thermal sensitivity of the compounds in the natural material.

In another preferred embodiment, the natural material as used in the preparation of the nanosuspension and provided in step a. of the method as disclosed above is pre-ground prior to and/or after the drying in a step a.1, preferably in a knife mill, and optionally sieved to a particle size ($D_{100}$) of less than 320 µm. Such grinding of the natural material may be done with the natural material as it is, i.e., without prior cutting or drying, or the natural material may be cut into pieces and/or dried as described above. Additionally, the natural material may be sieved in order to provide a powder of natural material having a particle size ($D_{100}$) of less than 320 µm.

An exemplary method for pre-grinding and sieving of a freeze-dried natural material may be as follows:

- The freeze-dried course natural material powder is put in a knife mill (e.g. Grindomix® 200 or 300 from Retsch GmbH, Germany) and ground with the following parameters: 10 sec at 2000 rpm following 10 sec at 5000 rpm and terminal 20 sec at 10.000 rpm;
- The course natural material powder from the knife mill process is sieved with a sieve of a mesh size of 320 µm;
- The natural material particles larger than 320 µm are again put in the knife mill for further grinding and following sieving with the 320 µm sieve. The residual of the second or third grinding step may be discarded.

Similarly, an exemplary method for pre-grinding and sieving of a thermally dried natural material may be as follows:

- The thermally dried natural material is cut into smaller pieces of about 1-2 cm with a knife;
- The 1-2 cm pieces are put in a knife mill (e.g. Grindomix® 200 or 300 from Retsch GmbH, Germany) and ground with the following parameters: 10 sec at 2000 rpm following 10 sec at 5000 rpm and terminal 20 sec at 10.000 rpm;
- The course natural material powder from the knife mill process is sieved with a sieve of a mesh size of 320 µm;
- The natural material particles larger than 320 µm are again put in the knife mill for further grinding and following sieving with the 320 µm sieve. The residual of the second or third grinding step may be discarded.

The at least one natural material having a particle size ($D_{100}$) of less than 320 µm provided in step a. is dispersed in a solvent in step b. according to the method of the present disclosure.

In another preferred embodiment, the solvent is water, preferably distilled water, or a mixture of water and ethanol.

The water used as solvent may be any kind of water, such as normal water, purified water, distilled water, bi- or tri-distilled water, or demineralized water. Similarly, also the ethanol used may be normal ethanol, or a mixture of water and ethanol. Accordingly, the resulting nanosuspension may be an aqueous nanosuspension, or a nanosuspension in ethanol, or a nanosuspension on the basis of a mixture of water and ethanol, or any other solvent or mixture of solvents. The term "solvent" as used herein refers to a single solvent or a mixture of solvents. Preferably, the solvent is a pharmaceutically acceptable solvent if the nanosuspension is used as a medicament.

In another preferred embodiment, the nanosuspension is an aqueous nanosuspension or a nanosuspension on the basis of a mixture of water and ethanol.

When dispersing the natural material in step b. in the solvent, the natural material preferably has a concentration in the range of from 0.5 to 20% (w/w), based on the total amount of solvent used, preferably from 2 to 10% (w/w), further preferably from 2 to 5% (w/w) or from 5 to 10% (w/w). In another preferred embodiment of the present application, the natural material preferably has a concentration in the range of from 0.5 to 70% (w/w), based on the total amount of solvent used, preferably from 40 to 70% (w/w), or from 10 to 40% (w/w). The concentration of the natural material in % (w/w) is based on the total amount of solvent used to prepare the nanosuspension. As an example, with 50 g powder of a natural material to 1000 g solvent, 5% (w/w) is prepared. Within said concentration range, the further milling of the suspension to a nanosuspension is eased. The dispersion may be prepared by stirring the solvent and the natural material, e.g., by means of a magnetic stirrer or any other rotating device, preferably with a speed of up to 1000 rpm.

Accordingly, in another preferred embodiment, the at least one natural material is dispersed in step b. in a concentration of from 0.5 to 20% (w/w), based on the total amount of the solvent used in the nanosuspension, preferably from 2 to 10% (w/w), further preferably from 2 to 5% (w/w) or from 5 to 10% (w/w).

In a particularly preferred embodiment, the at least one natural material is present in the nanosuspension at a concentration resulting in a solubility factor of above 0.4, or of above 0.5, or of above 0.8, or of above 1, or even of above 1.1.

It is preferred that the nanosuspension is stabilized by the use of a stabilizer. Such stabilizer may be selected from the group consisting of phospholipids, polysorbates, propane-1, 2,3-triol (glycerine), electrostatic or steric stabilizers and surfactants. Such stabilizers may be added to the dispersion in step b., or during the milling step c., or even after the milling step c. Some stabilizers are preferably added to the nanosuspension preferably in the dispersion step b., such as phospholipids, nonionic surfactants and emulsifiers, e.g. polysorbate. Other stabilizers are preferably added during the milling step c., like nonionic triblock copolymers, such as poloxamers. Even other stabilizers are preferably added after the milling step c., such as propane-1,2,3-triol or dioctyl sodium sulfosuccinate (DOSS) If a stabilizer is added in dispersion step b., it is preferred to add the stabilizer in an amount of 50% up to 200% (w/w), based on the total amount of natural material, in particular if the stabilizer is a phospholipid. If the stabilizers is a nonionic surfactant or an emulsifier, like polysorbate, it is preferably added in an amount of up to 1.5% (w/w), based on the amount of solvent. During the milling in step c., when specific particle sizes ($D_{90}$) in the range of 2 up to 10 µm have been reached, or if the particle size ($D_{90}$) is not further reduced during milling step c., e.g., by at least 4% during one hour milling time, or if the particle size ($D_{90}$) is increased during milling step c. by at least 10% during one hour milling time, it is preferred to add a stabilizer, like a nonionic triblock copolymer, such as poloxamers.

In a preferred embodiment, the stabilizer is selected from the group consisting of phospholipids; polysorbates; polymers, such as homopolymers, block and graft copolymers (like hydroxypropyl cellulose (HPC), hydroxypropyl methylcellulose (HPMC) and polyvinylpyrrolidone (PVP)); nonionic tri-block copolymers, such as poloxamers (e.g, Kolliphor® P407 or poloxamer 188); copolyvinylpyrrolidone; Labrasol®; Gelucire®; gelatin; lecithin (phosphatides); gum acacia; cholesterol; tragacanth; polyoxyethylene alkyl ethers; polyoxyethylene castor oil derivatives; polyoxyethylene sorbitan fatty acid esters; sorbitan fatty acid esters; polyethylene glycols; polyoxyethylene stearates; mono and diglycerides; colloidal silicon dioxide; sodium dodecylsulfate; magnesium aluminum silicate; triethanolamine; stearic acid; calcium stearate; glycerol monostearate; cetostearyl alcohol; cetomacrogol emulsifying wax; short and medium chain alcohols; Labrafil®; Purol-oleique®; propane-1,2,3-triol, polyvinyl alcohol and dioctyl sodium sulfosuccinate (DOSS). Preferred examples of polysorbates are polysorbate 80 and polysorbate 20. It is further preferred that the stabilizer is selected from the group consisting of polysorbate 80, polysorbate 20, Kolliphor® P407 and poloxamer 188. In a particularly preferred embodiment, the stabilizer is Kolliphor® P407, or polysorbate 80, such as Tween® 80. In another preferred embodiment, the dispersing step b. comprises the addition of a stabilizer selected from the group consisting of phospholipid and polysorbate.

In another preferred embodiment, the dispersing step b. comprises the addition of a polysorbate in an amount of from 0.5 to 2% (w/w), based on the total amount of the solvent used in the nanosuspension, and/or wherein the polysorbate is selected from the group consisting of polysorbate 80 and polysorbate 20.

In another preferred embodiment, the dispersing step b. comprises the addition of a phospholipid in an amount 100% to 200% (w/w), preferably in an amount of 130% to 170% (w/w), based on the amount of the natural material, preferably wherein the phospholipid contains up to 95% (by weight) phosphatidylcholine and from 20 to 30% (by weight) of lysophosphatidylcholine. It is preferred that the phospholipid contains 20-95% phosphatidylcholine, preferably 20-75% phosphatidylcholine, and 20-30% lysophosphatidylcholine (e.g. Lipoid P100, P75, R LPC20 of Lipoid GmbH, Germany). It may also be preferred to add the phospholipid in an amount of from 100 to 300% (w/w), more preferably from 50 to 200% (w/w), based on the total amount of the natural material.

When steric stabilizers are used as stabilizers, the steric stabilizer is adsorbed or attached onto the surface of the nano-particle and provides a large and dense steric barrier which overcomes attractive Van der Waals forces and hence the steric stabilizer reduces aggregation, agglomeration or even particle fusion. The steric stabilizers are preferably excipients which are pharmaceutically acceptable and may be selected from polymers, such as homopolymers, block and graft copolymers, like hydroxypropyl cellulose (HPC), hydroxypropyl methylcellulose (HPMC) and polyvinylpyrrolidone (PVP). A particularly preferred steric stabilizer is the nonionic tri-block copolymer Kolliphor® P407. Kolliphor® P407 is composed of a central hydrophobic chain of polyoxypropylene (poly(propylene oxide)) flanked by two hydrophilic chains of polyoxyethylene (poly(ethylene oxide)). It may be advantageous to add a steric stabilizer during the milling step c. Thus, it is preferred to add a steric stabilizer in an amount of from 0.5 to 2% (w/w) during the milling step c., further preferably when the particles have a particle size ($D_{90}$) of less than 5 μm.

Another preferred stabilizer used in the process of the present disclosure is glycerin (propane-1,2,3-triol). Said glycerin is preferably added after milling step c., further preferred in an amount of from 30 to 100% (v/v) or from 40 to 100% (v/v), even more preferably in an amount of 40% (v/v) or 50% (v/v), based on the total volume of the solvent.

In addition to glycerin, or in the alternative thereof, dioctyl sodium sulfosuccinate (DOSS) as electrostatic stabilizer may be used, preferably in an amount of from 0.5 to 2% (w/w), based on the total amount of the solvent, and added preferably after milling step c.

During milling step c., the dispersion containing the natural material at a particle size of less than 320 μm is milled to a particle size ($D_{90}$) of less than 1000 nm. This may be achieved in any suitable mill.

In a preferred embodiment, said milling step c. is carried out in a wet ball mill, preferably a wet ball agitator mill.

In a further preferred embodiment, said milling step c. comprises a first milling step c.1 in a wet ball mill, preferably a wet ball agitator mill, with a grinding ball diameter of from 0.5 to 1.5 mm, and a second milling step c.2 in a wet ball mill, preferably a wet ball agitator mill, with a grinding ball diameter of from 0.3 to 0.4 mm, and a third milling step c.2 in a wet ball mill, preferably a wet ball agitator mill, with a grinding ball diameter of from 0.05 to 0.2 mm. It is preferred that the second milling step c.2 is used until a particle size ($D_{90}$) of about 3 to 6 μm is reached, and the third milling step c.3 is used until a particle size ($D_{90}$) of about 80 to 500 nm, preferably 80 to 300 nm is reached. In another preferred embodiment with a starting particle size ($D_{100}$) of the natural material powder below 320 μm, said milling step c. comprises a first milling step c.1 in a wet ball mill, preferably a wet ball agitator mill, with a grinding ball diameter of from 0.4 to 0.5 mm, and a second milling step c.2 in a wet ball mill, preferably a wet ball agitator mill, with a grinding ball diameter of from 0.05 to 0.2 mm. It is preferred that the first milling step c.1 is used until a particle size ($D_{90}$) of about 2 to 6 μm is reached, and the second milling step c.2 is used until a particle size ($D_{90}$) of about 80 to 500 nm, preferably 80 to 300 nm is reached. It is furthermore preferred to have a temperature in the mill chamber of 25 to 36° C., and a rim speed of 10 to 14 m/s, preferably 11 to 14 m/s.

Accordingly, in a preferred embodiment, the dispersion of step b. is milled in step c. to a particle size ($D_{90}$) of below 500 nm ($D_{90}$<500 nm), preferably below 300 nm ($D_{90}$<300 nm), further preferably below 250 nm ($D_{90}$<250 nm), and most preferably below 200 nm ($D_{90}$<200 nm), as measured by a dynamic light scattering or laser diffraction analyzer.

The resulting nanosuspension may thus have a particle size ($D_{90}$) of below 500 nm ($D_{90}$<500 nm), preferably below 300 nm ($D_{90}$<300 nm), further preferably below 250 nm ($D_{90}$<250 nm), and most preferably below 200 nm ($D_{90}$<200 nm), as measured by a dynamic light scattering or laser diffraction analyzer, and a particle size of above 40 nm ($D_{90}$>40 nm).

The resulting nanosuspension may further be characterized for best stabilization results as a mono-modal suspension, wherein the single mode has an average value of smaller than 300 nm, preferably below 200 nm. Such mono-modal suspension may be achieved by filtering the suspension. The filter may reduce the particle size to a particle size ($D_{90}$) to below 450 nm, preferably below 300 nm, further preferably below 220 nm. As filter device any state of the art device can be used, such as a Sartorius Stedim Biotech filter. If the nanosuspension is filtered to 450 nm, such filtering makes the standard deviation of the particle size distribution even more narrow, which may contribute to the stabilization. In the alternative, a mono-modal suspension may also be achieved by corresponding processing means. As exemplified, the suspension of Example 12 is a mono-modal suspension without filtering.

During the milling step c., a certain specific energy is applied to the nanosuspension. The specific energy is defined as net energy (gross energy minus idling drive power) of the wet ball agitator mill in [kW] times the milling time in [h] divided by the total amount of the nanosuspension in [t] which is the amount of the solvent, natural material powder and all stabilizers in [t].

In an alternative to the chemical stabilization using stabilizers as disclosed above, the nanosuspension may also be physically stabilized by means of a colloidator (e.g. modified type Kamena from Levigata GmbH, Germany), as also depicted in FIG. 1. During this process, the nanosuspension is guided within a container (1) by the rotation of rotor (4) and the support rotor (5) into a concave cylinder (3) on its upper end via baffle plates in an almost turbulence free manner. In the interior concave cylinder (3), the descending nanosuspension stream (7) hits the counter rotating upward nanosuspension stream, excited by the rotors (4,5) at the exit at the lower end of the concave cylinder. At the collision of the descending stream of the nanosuspension and the antipodal rotating stream of the nanosuspension, the nano-particles are statically loaded by friction. This static load or particle charge may cause a separation of the nano-particles and therefore a physical stabilization. Thereafter, the nanosuspension rises (6) at the exterior hyperbolic cylinder in the reverse direction. The nanosuspension is hereby set in an upward and downward aligned movement. The thermal energy caused hereby is conducted by a water cooler integrated in the double wall (2) of the container (1), where the cooling medium is supplied to and diverted from the double wall (8a, 8b 9a, 9b).

Therefore, in a preferred embodiment, the nanosuspension is further subjected to a colloidation step d. in a colloidator following milling step c., preferably with the addition of oxygen. Such colloidation may furthermore replace the use of stabilizers, and in a further preferred embodiment, the nanosuspension does not contain any stabilizers, in particular it does not contain any propane-1,2,3-triol.

As described in detail above, the nanosuspension of the present disclosure may be chemically or physically stabilized.

The nanosuspension of the present disclosure may additionally contain oxygen ($O_2$). For the present disclosure, if water is enriched with oxygen, the oxygen may be dissolved in water, such as physically or chemically dissolved in the water, or adhere to any of the nano-particles. In order to enrich the nanosuspension with an extra amount of oxygen, the above described colloidator may be used. In an exemplary method of the present disclosure, about one minute after the start of the colloidation process, oxygen may be added until 20 to 30 mg/liter oxygen is contained in the nanosuspension. By this kind of process, the oxygen is added to the nanosuspension by a so called sucking process in contrast to the pressure method, where oxygen is inserted in a solution via pressure. As oxygen enrichment device, but not necessarily restricted to it, the ultra colloidator of Levigata Ltd. may be used.

In a preferred embodiment of the present disclosure, the nanosuspension has an oxygen concentration of from 20 to 30 mg/l.

In addition to the at least one natural material and the optional oxygen, the nanosuspension of the present disclosure may also comprise at least one compound selected from the group consisting of flavorings, preservatives, surfactants and permeation enhancers, such as riboflavin or ascorbic acid.

The nanosuspension may optionally be filtered in a filtering step after step c. and optionally prior to or after step d. With such filtering, the size of the nano-particles in the nanosuspension may further be adapted to the need. As an example, the sterile filtering of the nanosuspension may be mentioned. Such sterile filter may reduce the particle size to a particle size ($D_{90}$) to below 450 nm, preferably below 220 nm. As filter device any state of the art device can be used, such as a standard Milipore filter. If the nanosuspension is filtered to 220 nm, such filtering makes the standard deviation of the particle size distribution even more narrow, which may contribute to the stabilization.

In a preferred embodiment of the present disclosure, the nanosuspension is filtered after step c. and optionally prior to or after step d., preferably with a sterile filter, further preferably to a particle size below 450 nm, and more preferably below 220 nm.

Prior to use of the nanosuspension, the concentration of the nanosuspension may be adapted according to the needs. On the one hand, the nanosuspension may be diluted by the addition of further solvent. On the other hand, the concentration of the nanosuspension may be increased in a further step e. The increase of concentration may be achieved by evaporation of solvent, preferably in a drying chamber, further preferably at a temperature not exceeding 40° C., and optionally at reduced pressure. The final nanosuspension then preferably has a concentration of natural material in the range of from 10 to 40% (w/w), preferably of from 10 to 20% (w/w), based on the total amount of solvent present in the nanosuspension.

Therefore, in a preferred embodiment, the concentration of the nanosuspension is increased in a further step e. by evaporation of solvent, preferably in a drying chamber, to a concentration of the natural material of 10 to 40% (w/w), preferably to 10 to 20% (w/w), based on the total amount of solvent present in the nanosuspension.

Concluding from the above described method of preparation and supported by the examples in the experimental section, the nanosuspension of natural materials differs from an extract by the following factors:

Concentration of Active Components

Since the nanosuspension contains the whole or parts of the natural material in its natural composition as nano-particles, and not only extracted parts, such as water soluble compounds, the concentration of hydrophilic as well as hydrophobic compounds is higher in the nanosuspension compared to an extract. In an extract, only hydrophilic or hydrophobic compounds are in solution due to their solubility in the respective solvent.

Amount of Dry Mass

Due to the nature of a nanosuspension, the dry mass usually is the same or almost the same as the amount of compound added in step b. to form a nanosuspension. In contrast thereto, the dry mass of an extract is always less than the amount of compound put into a solvent, since the solubility of most compounds is considerably less than 100%.

Oxidation

Since nano-particles are usually dispersed in nanosuspensions with a limited solubility, the possibility of chemical reactions is not as substantial as that in solution-based formulations. Consequently, chemical stability of nanosuspensions is generally superior to that of solutions. The oxidation stability of a nanosuspension is attributed to a mechanism similar to oxidized layer on the aluminum surface. Monolayer degradation on the nano-particle surface is created once they were exposed to water and oxygen. This monolayer may protect the inner part of the nano-particles from further degradation, and thus enhance oxidation stability of the nanosuspensions.

Chemical Stabilization

The unique nano-scale structure of nano-particles provides significant increases in surface area to volume ratio which results in notably different behavior, both in-vitro and in-vivo, as compared to the traditional micro particles. Despite the advantages of drug nano-crystals, they present various drawbacks including complex manufacturing and stability issues. Stability is one of the critical aspects in ensuring safety and efficacy of drug products. In intravenously administered nanosuspensions, for example, formation of larger particles (>5 μm) could lead to capillary blockade and embolism, and thus drug particle size and size distribution needs to be closely monitored during storage. Such larger particles are excluded by the present nanosuspension.

Physical Stabilization

The particle charge is one of the factors determining the physical stability of nanosuspensions. The higher particles are equally charged, the higher is the electrostatic repulsion between the particles and the higher is the physical stability. Typically the particle charge is quantified as the so called zeta potential, which is measured e.g. via the electrophoretic mobility of the particles in an electrical field.

The above described method for the preparation of a nanosuspension results in a nanosuspension. Accordingly, the present disclosure also relates to a nanosuspension obtainable according to any one of the methods described herein.

Furthermore, the nanosuspension of the present disclosure may be used in the preparation of a medicament or supplement, such as a food supplement. The nanosuspension of the present disclosure may advantageously be used in the preparation of a medicament for buccal, topical and/or oral application to an animal, preferably a human.

Nanosuspensions of natural materials offer distinct advantages including the possibility to be administered via the trans-mucosal route. The nanosuspensions of natural materials contain a higher concentration of active agents per volume unit, smaller particles of non-water soluble active agents and provide therefore new possibilities for immune-modulating drugs, where immune-modulating active agents are taken-up by immune cells, which require small particle size of the immune-modulating active agents.

For oral cavity administration, the drug should preferably be liquid and efficacious in low dosages since the uptake capacity of substances via the oral cavity is limited. Furthermore the particles of a drug administered via the oral cavity should be in the nanometer range, e.g., less than approx. 300 nm, otherwise the passage through the oral cavity is limited. Since the nanosuspension of the present disclosure may be provided with a particle size $D_{90}$ below 300 nm, the nanosuspension may advantageously be used for oral cavity administration.

Within the oral cavity, there are two generally recognized routes of administration of a biologically active agent. Sublingual delivery is achieved through the mucosal membranes lining the floor of the mouth. Due to the high permeability and the rich blood supply, transport via the sublingual route results in a rapid onset of action, providing a delivery route appropriate for highly permeable active agents with short delivery period requirements and an infrequent dosing regimen. The second generally recognized route is via the buccal mucosa. This area encompasses the mucosal membranes of the inner lining of the cheeks. This area also has a rich blood supply, is robust, and provides a short cellular recovery time following stress or damage. Although the buccal mucosa is less permeable than the sublingual area, the expanse of smooth and relatively immobile mucosa provides a highly desirable absorption pathway for sustained-release and controlled-release delivery of biologically active agents. As with other trans mucosal routes of administration, two major advantages include avoiding hepatic first-pass metabolism and pre-systemic elimination within the gastro intestinal tract.

Additionally, any known permeation enhancer can increase the passage of a nanosuspension according to the present disclosure.

Apart from oral administration, the nanosuspensions of the present disclosure may also be used for parenteral, intrathecal, intravenous, transdermal, or trans mucosal application to an animal, preferably a human. Accordingly, a preferred embodiment of the present disclosure relates to the use of a nanosuspension in the preparation of a medicament for parenteral, intrathecal, intravenous, transdermal, or trans mucosal application, preferably buccal, topical or oral application, to an animal, preferably a human.

The present disclosure provides a stable nanosuspension of natural materials, methods of preparing said nanosuspensions and to the use of said nanosuspensions, which enable enhanced delivery of the biologically active agents into the bloodstream of a subject. Upon contact of such nanosuspension with the body, e.g. with an area of the oral cavity including the buccal mucosa, the compound is absorbed into the bloodstream in an amount sufficient to elicit a desired biological response. Accordingly, the nanosuspensions can be delivered by way of a normal or microfluidized spray, an aerosol or a liquid. Delivery may be accomplished by parenteral, intrathecal, intravenous, transdermal, trans mucosal, and any or all commonly recognized methods for drug delivery.

The most significant differentiating factors for a nanosuspension prepared according to the methods disclosed herein compared to, e.g., an extract are (i) the mean molar mass of the main active components of the natural material—the lower the mean molar mass, the higher the bioavailability, (ii) the grade of recognition of the main active components of the natural material in the human organism by specific human receptors (so called pathogen recognition receptors or toll like receptors TLR; only if the grade of detection by TLR is high, an increased immune stimulating effect can be initialized by the following signal cascade), and (iii) the resulting effect of the main active components of the natural material in the human organism. For the natural material *agaricus subrufescens* these differentiating factors are presented in the Examples 7 to 9 below using β-1,3/1,6-glucan as the main active component of *agaricus subrufescens*, which is water insoluble.

The nanosuspensions of the present disclosure may be used in the treatment or prevention of cancer, inflammatory bowel disease (IBD), arthritis, human immunodeficiency virus (HIV), other viral diseases, dermatological diseases, such as neurodermatitis or psoriasis, or auto-immune diseases, such as multiple sclerosis, vasculitis, rheumatoid arthritis or dermatomyositis.

The nanosuspensions of the present disclosure are effective in providing higher concentrations of the active agents of natural materials in the bloodstream over a longer period of time as compared to e.g. extracts prepared from the natural materials. This especially applies to hydrophobic compounds contained in such natural materials. Furthermore, nanosuspensions containing immune-modulatory compounds from natural materials stimulate the immune system in a broader and more intense manner, since they contain more immune stimulating particles in the nanometer range and higher amount, which are better taken up or recognized by the respective immune subpopulation compared to, e.g., extracts.

EXPERIMENTAL SECTION

In the following, the present invention is illustrated in more detail. However, it is understood that the scope of protection is only determined by the attached claims, not being restricted to any of the following Examples. The following Examples are set forth to assist in understanding the invention and should not be construed as specifically limiting the invention described and claimed herein. Such variations of the invention, including the substitution of all equivalents now known or later developed, that would be within the purview of those skilled in the art, and changes in formulation or changes in experimental design, are to be considered to fall within the scope of the invention incorporated herein.

Example 1

Example 1.1

Figure 2:
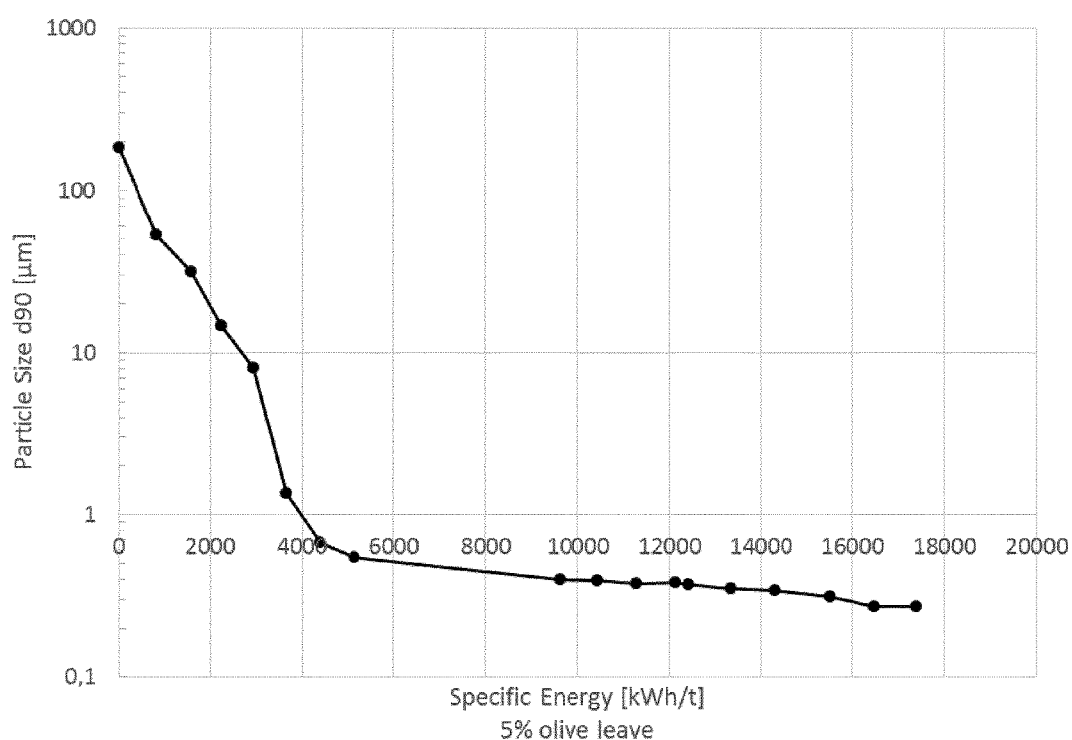
FIG. 2: shows the particle size ($D_{90}$) for a nanosuspension of olive leaves at a specific energy used for milling according to Example 1.1.

Stable Formulation of an Olive Leaf Nanosuspension 200 g dry olive leave powder (particle size $D_{90}$: <320 µm, residual moisture <5%) was added to 4000 g bi-distilled water, resulting in a 5% (w/w) dispersion of olive leave powder in water. The solubility of olive leave powder with a particle size of $D_{90}$<320 µm is 1.44% (w/w). Based thereon, the concentration of the nanosuspension of 5% (w/w) is a factor of 3.5 (solubility factor) above the solubility limit of olive leave powder. The dispersion was milled to a particle size ($D_{90}$) of below 400 nm in a wet ball agitator mill (type X1, Buehler AG, Switzerland) using yttrium stabilized zirconia balls of size 0.4 to 0.5 mm until the particle size ($D_{90}$) is about 380 nm, and then using yttrium stabilized zirconia balls of size 0.1 mm until the final particle size ($D_{90}$) of 272 nm is reached. At a particle size ($D_{90}$) of 380 nm, 14.5 g (0.4° A (w/w)) Tween® 80 was added. This reduced the particle size down to 340 nm. A further add-on of 29 g (0.7% (w/w)) Kolliphor® P407 at a particle size ($D_{90}$) of about 340 nm significantly reduced the particle size ($D_{90}$) to 272 nm (see FIG. 2). The amount of specific energy [kWh/t] used for the milling can be seen from FIG. 2.

Example 1.2

Extraction of an Olive Leave (Comparative)

The same amount of olive powder (200 g, particle size $D_{90}$: <320 µm) was extracted in 4000 g bi-distilled water for 2 hours at a temperature of 22° C.

Example 1.3

Dry Mass Comparison

Figure 3:
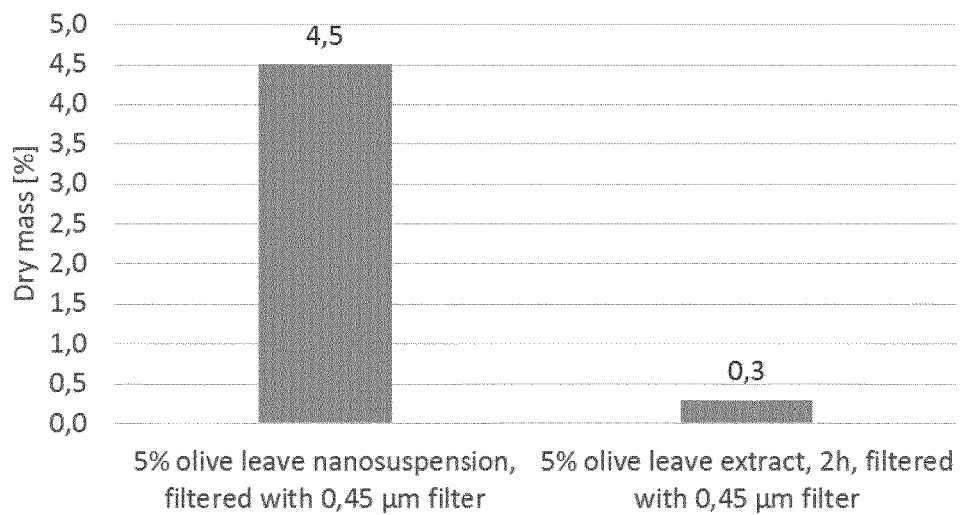
FIG. 3 shows the dry mass of an extract and of a nanosuspension of olive leaves according to Example 1.3.

The amount of dry mass of the extract (Example 1.2) and the nanosuspension (Example 1.1) as prepared above was determined by filtering the extract and nanosuspension, respectively, with a 0.45 µm filter (Millipore, cellulose ester membrane). The filtered solids were dried and the dry mass of the filtered particles was determined. As can also be seen from FIG. 3, the amount of dry mass of the nanosuspension is 4.5% (w/w) compared to 0.3% (w/w) of the extract with the same concentration of olive leave powder (5% (w/w)).

Example 2

Example 2.1

Figure 4:
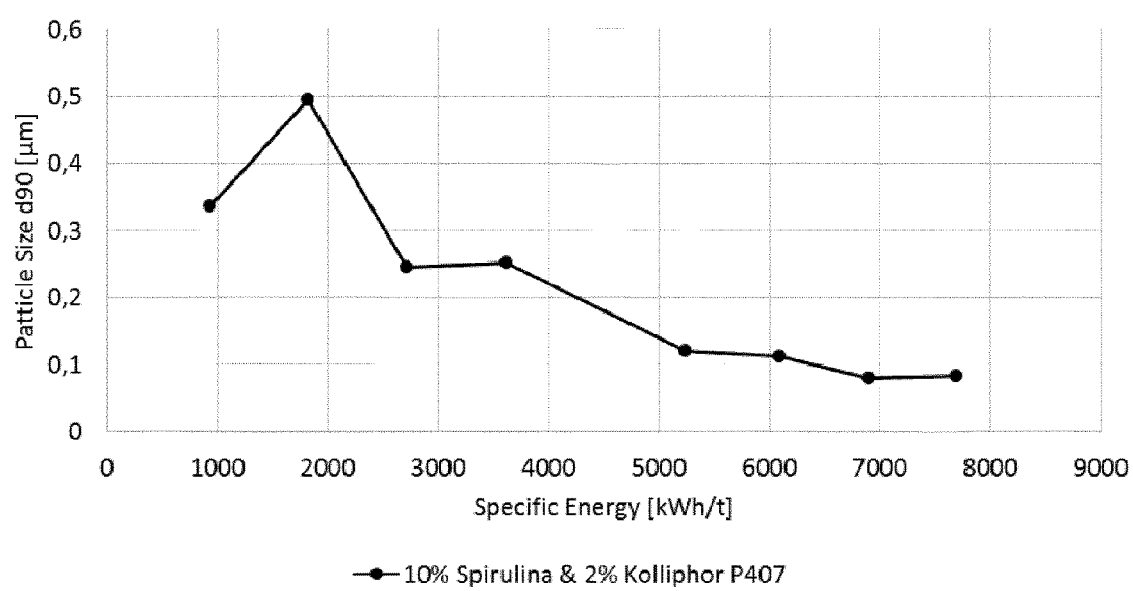
FIG. 4: shows the particle size ($D_{90}$) for a nanosuspension of spirulina at a specific energy used for milling according to Example 2.1.

Stable Formulation of a Spirulina Nanosuspension 300 g spirulina powder (10% (w/w), particle size $D_{90}$: <150 µm, residual moisture <5%) and 60 g Kolliphor® P407 were added to 3000 g bi-distilled water, resulting in a dispersion of spirulina in water. The solubility of spirulina powder with a particle size of $D_{90}$<150 µm is 0.52% (w/w). Based thereon, the concentration of the nanosuspension of 10% (w/w) is a factor of 19.2 (solubility factor) above the solubility limit of spirulina powder. The dispersion was milled to a particle size ($D_{90}$) of about 80 nm in a wet ball agitator mill (type X1, Buehler AG, Switzerland) using yttrium stabilized zirconia balls of size 0.4 to 0.5 mm until the particle size ($D_{90}$) is about 120 nm, and then using yttrium stabilized zirconia balls of size 0.1 mm until the final particle size ($D_{90}$) of 80 nm. The amount of specific energy [kWh/t] used for the milling can be seen from FIG. 4.

Example 2.2

Extraction of a Spirulina (Comparative)

The same amount of spirulina powder (300 g, particle size $D_{90}$: <150 µm) was extracted in 3000 g bi-distilled water for 2 hours at a temperature of 22° C.

Example 2.3

Dry Mass Comparison

Figure 5:
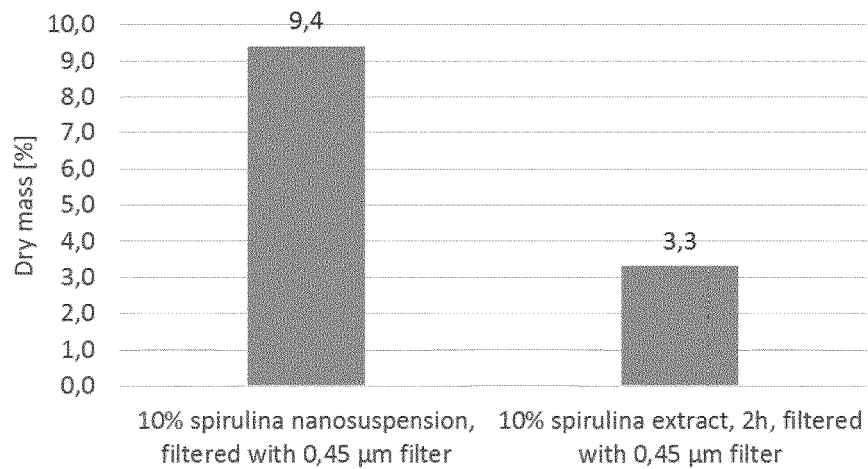
FIG. 5 shows the dry mass of an extract and of a nanosuspension of spirulina according to Example 2.3.

The amount of dry mass of the extract (Example 2.2) and the nanosuspension (Example 2.1) as prepared above was determined by filtering the extract and nanosuspension, respectively, with a 0.45 µm filter (Millipore, cellulose ester membrane). The filtered solids were dried and the dry mass of the filtered particles was determined. As can also be seen from FIG. 5, the amount of dry mass of the nanosuspension is 9.4% (w/w) compared to 3.3% (w/w) of the extract with the same concentration of spirulina powder (10% (w/w)).

Example 3

Example 3.1

Stable Formulation of an *Agaricus Subrufescens* Mushroom Nanosuspension with 5% P100, 0.5% Tween® 80 and 1% Kolliphor P407

Figure 6:
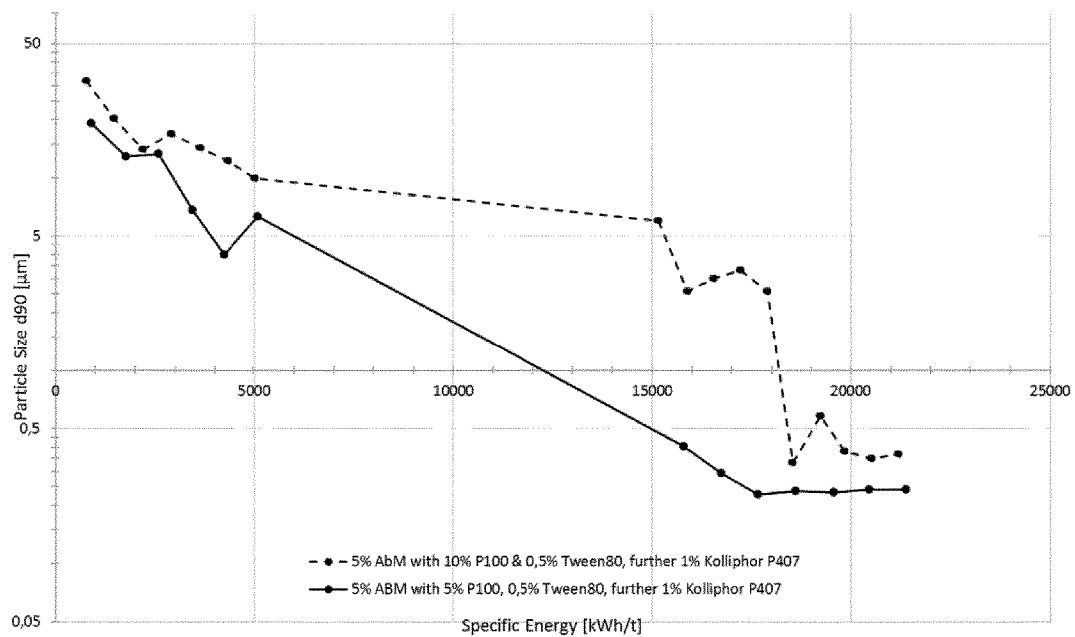
FIG. 6 shows the particle size ($D_{90}$) for a nanosuspension of *agaricus subrufescens* (ABM) at a specific energy used for milling according to Examples 3.1 (solid line) and 3.2 (dashed line)

150 g powder of *agaricus subrufescens* (particle size $D_{90}$: <320 µm, residual moisture <5%), 150 g Lipoid P100 (5% (w/w)) and 15 g polysorbate Tween® 80 (0.5% (w/w)) were added to 3000 g bi-distilled water, resulting in a 5% (w/w) dispersion of *agaricus subrufescens* powder in water. The solubility of *agaricus subrufescens* powder with a particle size of $D_{90}$<320 µm is 3.2% (w/w). Based thereon, the concentration of the nanosuspension of 5% (w/w) is a factor of 1.6 (solubility factor) above the solubility limit of *agaricus subrufescens* powder. The dispersion was milled in a wet ball agitator mill (type X1, Buehler AG, Switzerland) using yttrium stabilized zirconia balls of size 0.4 to 0.5 mm until the particle size ($D_{90}$) is about 6.3 µm, and then using yttrium stabilized zirconia balls of size 0.1 mm until the final particle size ($D_{90}$) of 240 nm is reached. The amount of specific energy [kWh/t] used for the milling can be seen from FIG. 6 (solid line). At a particle size ($D_{90}$) of about 6.3 μm, 30 g (1% (w/w)) Kolliphor® P407 was added. The final particle size ($D_{90}$) of the nanosuspension was 240 nm (see also FIG. 6—solid line).

Example 3.2

Stable Formulation of an *Agaricus Subrufescens* Mushroom Nanosuspension 10% P100, 0.5% Tween® 80 and 1% Kolliphor P407

150 g powder of *agaricus subrufescens* (particle size $D_{90}$: <320 μm), 300 g Lipoid P100 (10% (w/w)) and 15 g polysorbate Tween® 80 (0.5% (w/w)) were added to 3000 g bi-distilled water, resulting in a 5% (w/w) dispersion of *agaricus subrufescens* powder in water. The dispersion was milled in a wet ball agitator mill (type X1, Buehler AG, Switzerland) using yttrium stabilized zirconia balls of size 0.4 to 0.5 mm until the particle size ($D_{90}$) is about 6.3 μm, and then using yttrium stabilized zirconia balls of size 0.1 mm until the final particle size ($D_{90}$) of 368 nm is reached. The amount of specific energy [kWh/t] used for the milling can be seen from FIG. 6 (dashed line). At a particle size ($D_{90}$) of about 2.6 μm, 30 g (1% (w/w)) Kolliphor® P407 was added. The final particle size ($D_{90}$) of the nanosuspension was 368 nm (see also FIG. 6—dashed line).

Example 3.3

Stable Formulation of an *Agaricus Subrufescens* Mushroom Nanosuspension 5% P100, 0.75% Tween® 80

Figure 7:
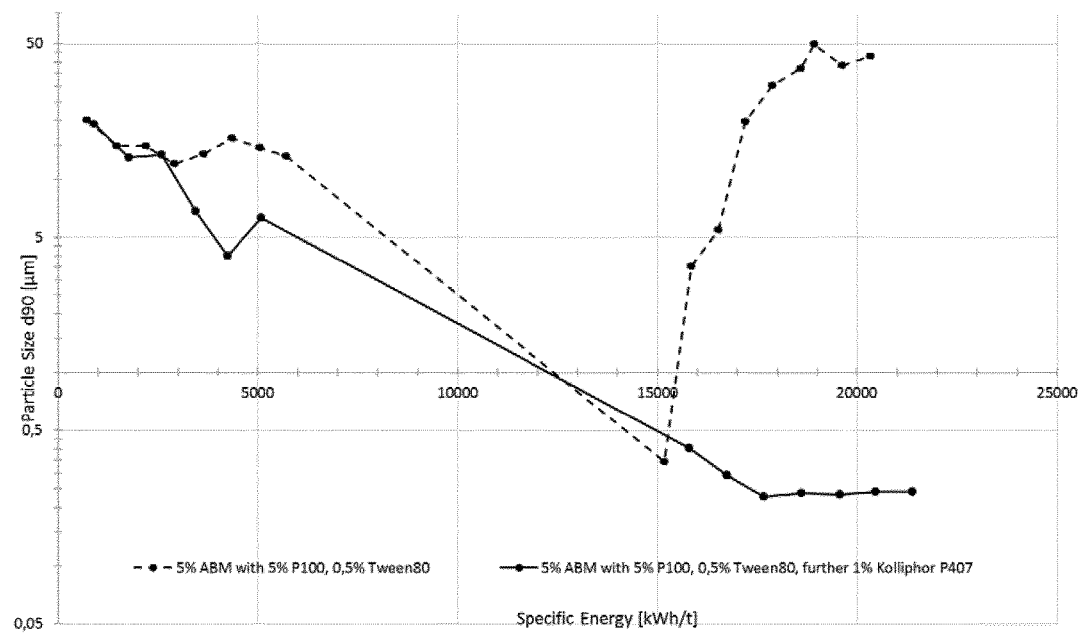
FIG. 7 shows the particle size ($D_{90}$) for a nanosuspension of *agaricus subrufescens* (ABM) at a specific energy used for milling according to Examples 3.1 (solid line) and 3.3 (dashed line)

150 g powder of *agaricus subrufescens* (particle size $D_{90}$: <320 μm), 150 g Lipoid P100 (5% (w/w)) and 15 g polysorbate Tween® 80 (0.5% (w/w)) were added to 3000 g bi-distilled water, resulting in a 5% (w/w) dispersion of *agaricus subrufescens* powder in water. The dispersion was milled in a wet ball agitator mill (type X1, Buehler AG, Switzerland) using yttrium stabilized zirconia balls of size 0.4 to 0.5 mm. The amount of specific energy [kWh/t] used for the milling can be seen from FIG. 7 (dashed line). The particle size ($D_{90}$) of the nanosuspension was reduced to 343 nm at a specific energy of 15170 kWh/t (see also FIG. 7—dashed line). After continued milling at increased specific energy, the particle size suddenly increased, probably due to a high surface area of the particle, which may be a cause of agglomeration. Even the add-on of further 7.5 g polysorbate Tween® 80 (resulting in a total of 0.75% (w/w)) did not significantly reduce the particle size. In comparison, the same nanosuspension but with an additional 1% Kolliphor® P407 (Example 3.2 above) and 0.5% polysorbate Tween® 80 shows a further decrease of the particle size and also stabilization (see FIG. 7—solid line).

Example 3.4

Extraction of an *Agaricus Subrufescens* Mushroom (Comparative)

The same amount of *agaricus subrufescens* powder (150 g, particle size $D_{90}$: <320 μm) was extracted in 3000 g bi-distilled water for 2 hours at a temperature of 22° C.

Example 3.5

Dry Mass Comparison

Figure 8:
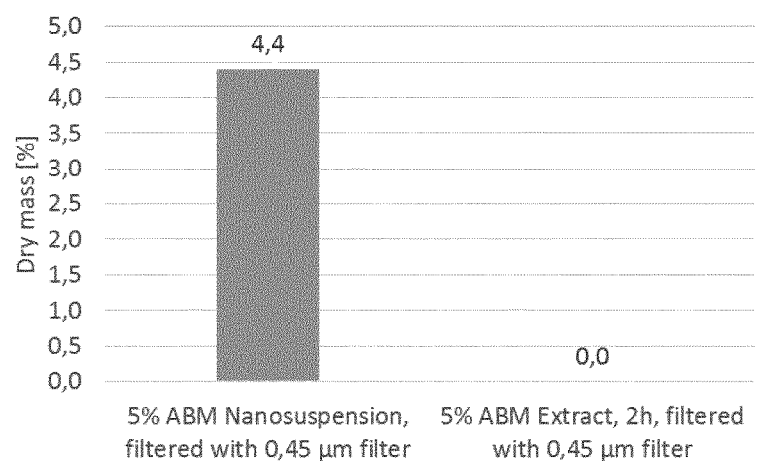
FIG. 8 shows the dry mass of an extract and of a nanosuspension of *agaricus subrufescens* (ABM) according to Example 3.5.

The amount of dry mass of the extract (Example 3.4) and the nanosuspension (Example 3.1) as prepared above was determined by filtering the extract and nanosuspension, respectively, with a 0.45 μm filter (Millipore, cellulose ester membrane). The filtered solids were dried and the dry mass of the filtered particles was determined. As can also be seen from FIG. 8, the amount of dry mass of the nanosuspension is 4.4% (w/w) compared to 0% (w/w) of the extract with the same concentration of *agaricus subrufescens* powder (5% (w/w)).

Example 4

Example 4.1

Concentration of Active Components

The leading active agent of *agaricus subrufescens* is β-1,3/1,6-glucan, and this glucan may therefore be used as reference material to compare the concentration of different extracts of *agaricus subrufescens* and a nanosuspension of *agaricus subrufescens*. Apart from the 5% (w/w) nanosuspension of Example 3.1 and the 5% (w/w) extract of *agaricus subrufescens* of Example 3.4, further extracts were prepare in an analogous manner to Example 3.4. The other extract types in FIG. 9 where all done with the same parameters (150 g *agaricus subrufescens* powder to 3000 g solvent, extraction time for 2 h) with different solvents (bi-distilled water and 60% (v/v) ethanol (EtOH)) and different temperatures (room temperature 22° C. and 80° C.), as indicated in FIG. 9.

Figure 9:
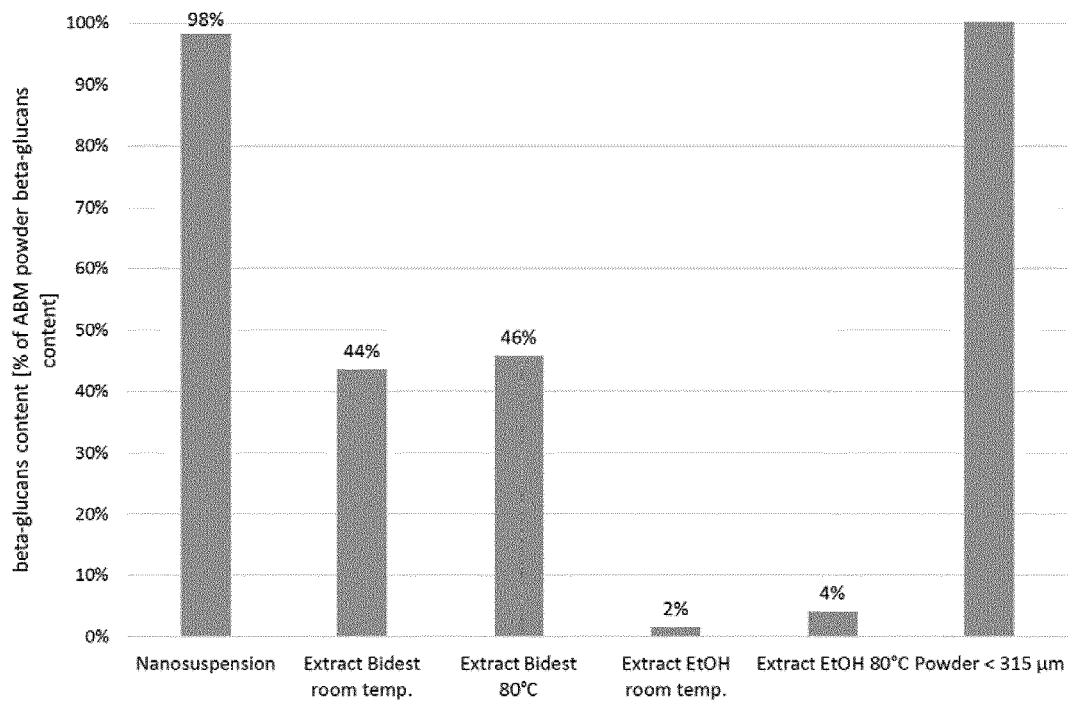
FIG. 9: shows the β-glucan content of a nanosuspension and different extracts of *agaricus subrufescens*, in relation to a powder of *agaricus subrufescens* as prepared in Example 4.1.

FIG. 9 shows the comparison of the β-1,3/1,6-glucan content for different extracts of *agaricus subrufescens* powder, and the nanosuspension of Example 3.1, in relation to the pure *agaricus subrufescens* powder used for the preparation of the extracts and the nanosuspension. In the nanosuspension, 98% of the β-1,3/1,6-glucan content of the powder is incorporated, compared to only 2% of the ethanol extract at room temperature and up to 46% at 80° C. in bi-distilled water.

This shows that in the nanosuspension almost all β-1,3/1,6-glucan from the powder fraction are retained.

Example 5

Example 5.1

Figure 10:
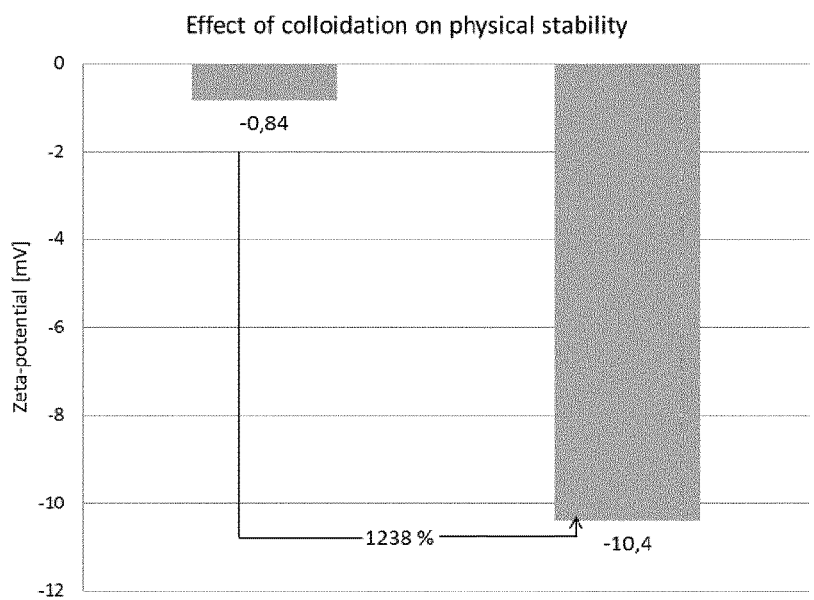
FIG. 10: shows the effect of physical stabilization on the basis of a silica nanosuspension as prepared in Example 5.1.

Stable Formulation of a Silica Nanosuspension 100 g silica powder (particle size $D_{90}$: <25 nm) were added to 2000 g bi-distilled water, resulting in a 5% (w/w) dispersion of silica powder in water. The silica nanosuspension was stabilized with the physical stabilization described in detail above. The zeta potential, measured by the laser diffraction analyzer Zetasizer (Malvern Instruments, UK) was taken as physical parameter to assess the effect of the physical stabilization. Accordingly, the zeta potential was measured prior to and after physical stabilization with the colloidator. Due to the physical stabilization in the colloidator for 3 minutes at 3000 $min^{-1}$ the zeta potential was reduced from −0.84 mV to −10.4 mV. This is a significant reduction compared to the value without physical stabilization (see FIG. 10).

Example 6

In Example 6, different nanosuspensions were tested for their long-term stability. An accelerated stability test was done with an analytical centrifuge (Lumifuge of LUM GmbH, Germany) to classify and quantify the de-mixing phenomena, like sedimentation, flotation or consolidation, of the nanosuspension. This test was used to determine the stability of the nanosuspension. A nanosuspension is considered long-term stable if there is no or only some sedimentation, flotation or consolidation of nanoparticles.

In the accelerated stability test, the nanosuspension was accelerated in the centrifuge with 2000 g (g=force of gravity constant=9.81 m/s$^2$). With the help of the Lumifuge space- and time-resolved extinction profiles over the entire sample length were obtained. Parallel light ($I_0$) illuminates the entire sample cell and the transmitted light I is detected by thousands of sensors arranged linearly across the whole sample from top to bottom with a microscale resolution. Transmission is converted into extinction by lg ($I/I_0$), and particle concentration may be calculated.

In order to achieve a long term stable nanosuspension, propane-1,2,3-triol may be added to increase the viscosity of the nanosuspension and prevent the sedimentation of the nanoparticles in the nanosuspension. The following Examples show the effect of addition of propane-1,2,3-triol.

Example 6.1

Long Term Stable Formulation of an *Agaricus Subrufescens* Mushroom Nanosuspension with 0% Propane-1,2,3-Triol The nanosuspension as prepared in Example 3.1 was taken and stirred for about 30 minutes with a magnetic stirrer, without addition of propane-1,2,3-triol. Then, an accelerated stability test was done with an analytical centrifuge (Lumifuge of LUM GmbH, Germany) to classify and quantify the de-mixing phenomena, like sedimentation, flotation or consolidation, of the nanosuspension, as described above.

Figure 11:
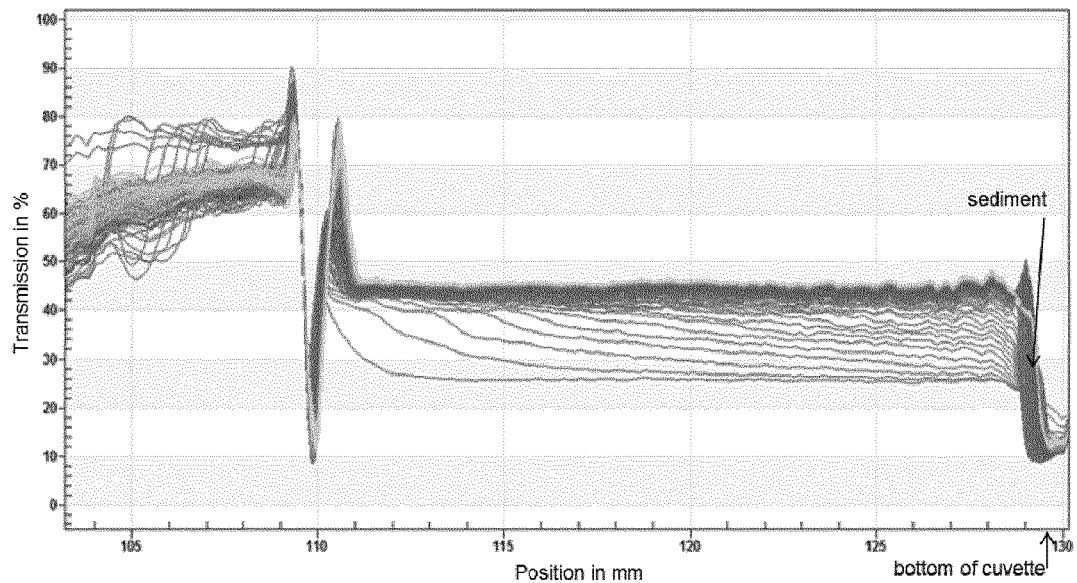
FIG. 11: shows the effect of chemical stabilization without propane-1,2,3-triol on the basis of a nanosuspension of *agaricus subrufescens* as prepared in Example 3.1.

FIG. 11 shows the light transmission curve of the nanosuspension with 0% propane-1,2,3-triol. As can be seen, larger particles sediment under the 2000 g field in the first revolution (light grey lines between 40% and about 25% transmission), then further larger particles follow in the next revolutions until after 20 minutes a sediment is formed at the bottom of the cuvette. The transmission rate decreases from 44% at the beginning down to 10% (sediment at the bottom of the cuvette), illustrating the sedimentation process under the 2000 g field. This shows the long term instability of the nanosuspension.

Example 6.2

Long Term Stable Formulation of an *Agaricus Subrufescens* Mushroom Nanosuspension with 20% Propane-1,2,3-triol 500 ml of the nanosuspension as prepared in Example 3.1 was taken and 20% (v/v) propane-1,2,3-triol was added. The resulting mixture was stirred for about 30 minutes with a magnetic stirrer. Then, the above described accelerated stability test was done.

Figure 12:
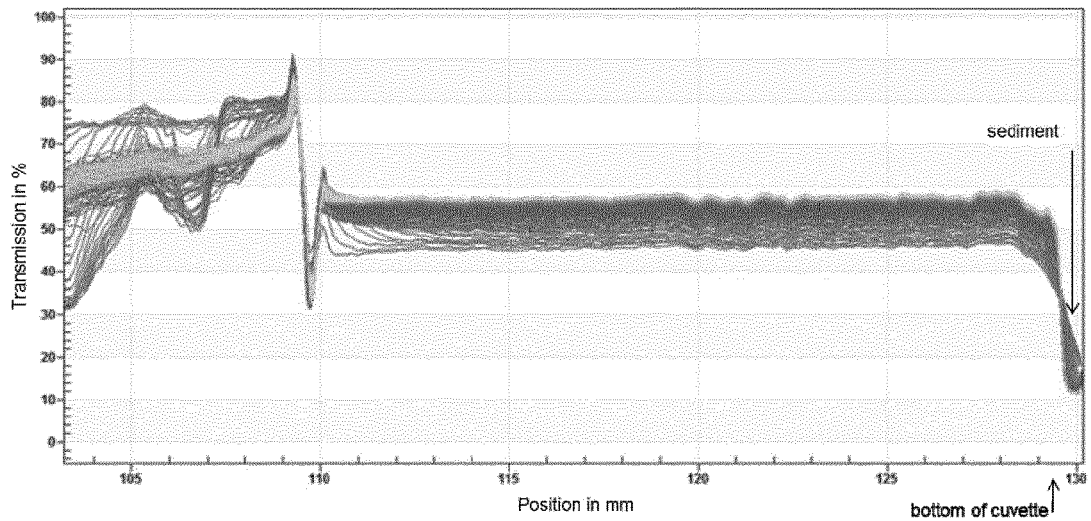
FIG. 12: shows the effect of chemical stabilization with 20% (v/v) propane-1,2,3-triol on the basis of a nanosuspension of *agaricus subrufescens* as prepared in Example 3.1.

FIG. 12 shows the light transmission curve of the nanosuspension with 20% propane-1,2,3-triol. As can be seen, the amount of larger particles (light grey lines between 50% and 40% transmission) that sediment under the 2000 g field is much lower in the first revolutions, until after 20 minutes a sediment is formed at the bottom of the cuvette. The transmission rate decreases from 58% as at the beginning down to 10% (sediment at the bottom of the cuvette), illustrating the sedimentation process under the 2000 g field. This shows that by the adding 20% (v/v) propane-1,2,3-triol the stability of the nanosuspension may be increased.

Example 6.3

Long Term Stable Formulation of an *Agaricus Subrufescens* Mushroom Nanosuspension with 50% Propane-1,2,3-Triol 500 ml of the nanosuspension as prepared in Example 3.1 was taken and 50% (v/v) propane-1,2,3-triol was added. The resulting mixture was stirred for about 30 minutes with a magnetic stirrer. Then, the above described accelerated stability test was done.

Figure 13:
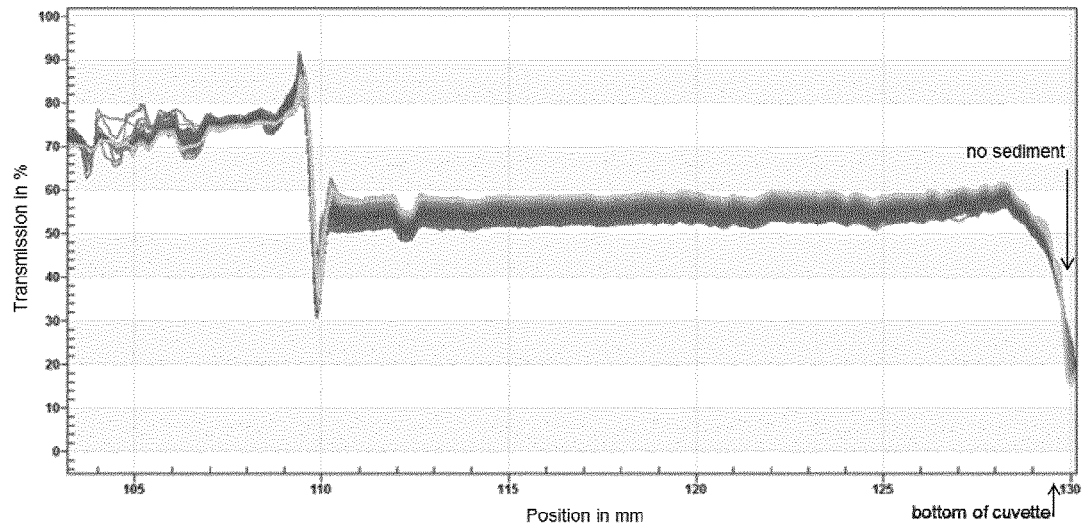
FIG. 13: shows the effect of chemical stabilization with 50% (v/v) propane-1,2,3-triol on the basis of a nanosuspension of *agaricus subrufescens* as prepared in Example 3.1.

FIG. 13 shows the light transmission curve of the nanosuspension with 50% propane-1,2,3-triol. As can be seen, there is no sedimentation during the 20 minutes under the 2000 g field (light grey lines between 50% and about 53% transmission). There is no sediment at the bottom of the cuvette. This shows that by the adding 50% (v/v) propane-1,2,3-triol, the stability of the nanosuspension is further increased.

Example 7

Figure 14:
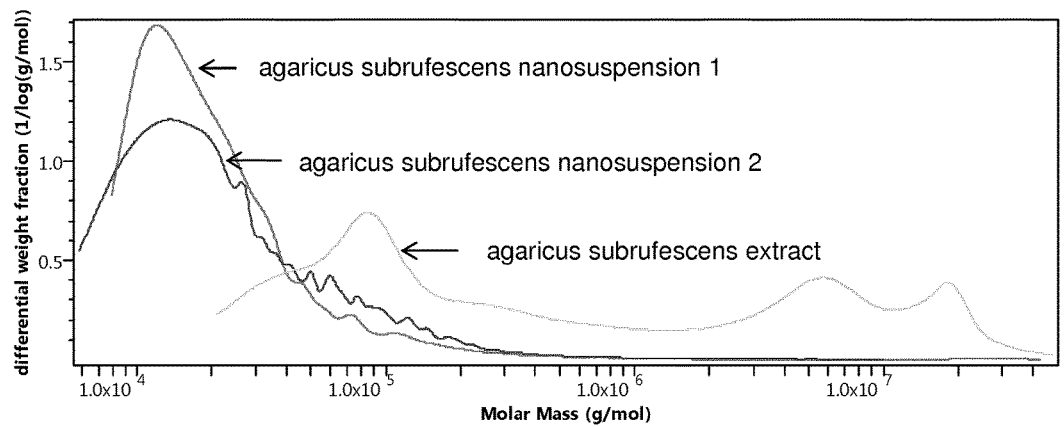
FIG. 14: shows the differential weight fraction (i.e., mean molar mass) of β-1,3/1,6-glucan of a 5% (w/w) *agaricus subrufescens* nanosuspension (as prepared in Example 3.1) and a 5% (w/w) *agaricus subrufescens* extract (as prepared in Example 3.4).

Mean Molar Mass of β-1,3/1,6-glucan of *Agaricus Subrufescens* Mushroom Nanosuspension and Extract Both with 5% (w/w) Concentration FIG. 14 shows the differential weight fraction (i.e., mean molar mass) of β-1,3/1,6-glucan of the *agaricus subrufescens* nanosuspension as prepared in Example 3.1 and the extract as prepared in Example 3.4 (nanosuspension 1: 20 μl injected volume in detector; nanosuspension 2: 10 μl injected volume in detector, extract: 10 μl injected volume in detector). The molar mass of the *agaricus subrufescens* nanosuspension was measured with two injected volumes in order to show the reliability of the analytical method, which showed to be stable. The mean molar mass of the active substance β-1,3/1,6-glucan of the *agaricus subrufescens* nanosuspension is between 15 and 16 kDa and that of the extract is 135 kDa. This shows that the method to prepare a nanosuspension from natural materials described herein reduces the molar mass of the main active substance β-1,3/1,6-glucan significantly. This results in a higher resorption of the β-1,3/1,6-glucan present in the nanosuspension when administered.

Example 8

Figure 15:
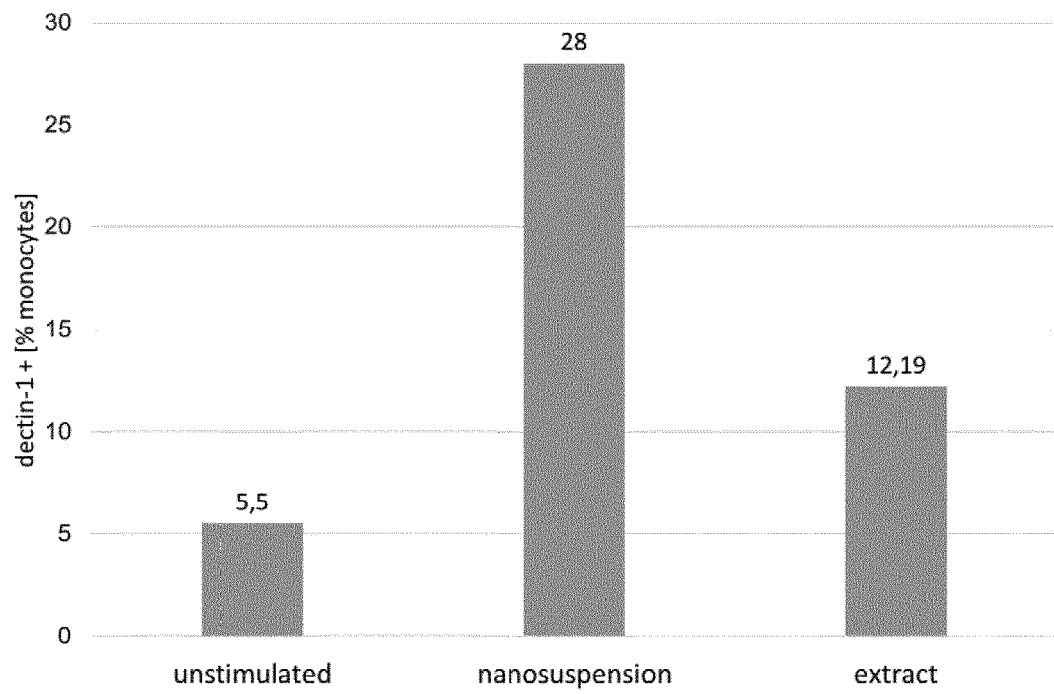
FIG. 15: shows the relative amount of dectin-1 positive monocytes (in %) in a sample of unstimulated peripherial blood mononuclear cells (PBMC), PBMC stimulated with 5% (w/w) *agaricus subrufescens* nanosuspension (as prepared in Example 3.1) and 5% (w/w) *agaricus subrufescens* extract (as prepared in Example 3.4).

Detection of β-1,3/1,6-glucan of *Agaricus Subrufescens* Mushroom Nanosuspension and Extract Both with 5% (w/w) Concentration Dectin-1 is the main receptor on immune cells which detects β-1,3/1,6-glucan in the human organism. FIG. 15 shows the relative amount of dectin-1 positive monocytes (in %) in a sample of unstimulated peripherial blood mononuclear cells (PBMC), PBMC stimulated with 5% (w/w) *agaricus subrufescens* nanosuspension (as prepared in Example 3.1) and 5% (w/w) *agaricus subrufescens* extract (as prepared in Example 3.4), respectively. The number of PBMC is increased by 409% when stimulated with 5% (w/w) *agaricus subrufescens* nanosuspension in relation to an unstimulated sample, compared to an increase of 122% at a stimulation with 5% (w/w) *agaricus subrufescens* extract.

Example 9

Figure 16:
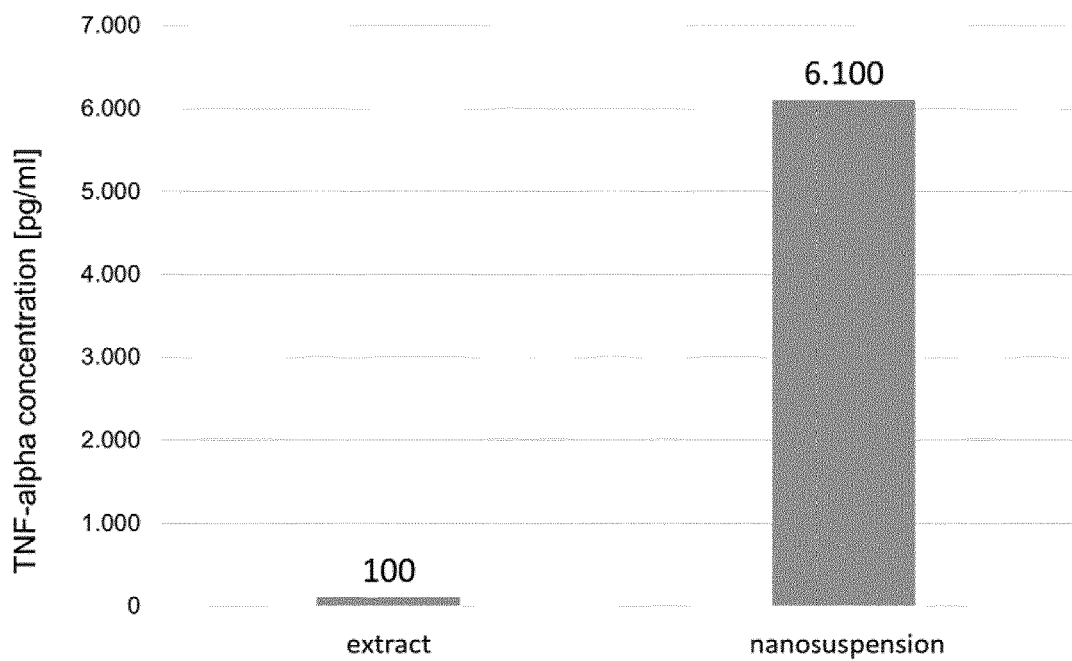
FIG. 16: shows the comparison of in-vitro induction of cytokine TNF-alpha caused by a 5% (w/w) *agaricus subrufescens* nanosuspension (as prepared in Example 3.1) and a 5% (w/w) extract (as prepared in Example 3.4).

Induction of Cytokine TNF-alpha by *Agaricus Subrufescens* Mushroom Nanosuspension and Extract Both with 5% (w/w) Concentration TNF-alpha is one of the major cytokines in disease development. FIG. 16 shows the comparison of in-vitro induction of cytokine TNF-alpha caused by *agaricus subrufescens* nanosuspension (as prepared in Example 3.1) and extract (as prepared in Example 3.4). The induction of TNF-alpha by *agaricus subrufescens* nanosuspension is by a factor of 60 higher compared to the extract.

Example 10

Figure 17:
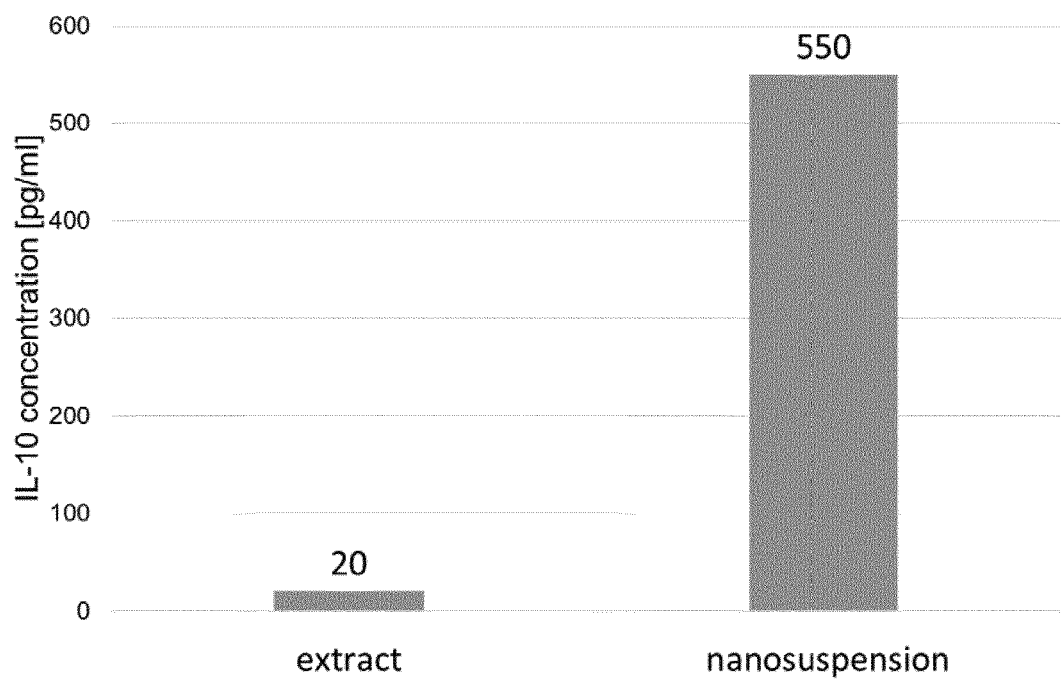
FIG. 17: shows the comparison of the cytokine IL-10 in an in-vitro induction caused by a 5% (w/w) *agaricus subrufescens* nanosuspension (as prepared in Example 3.1) and a 5% (w/w) extract (as prepared in Example 3.4).

Induction of Cytokine IL-10 by *Agaricus Subrufescens* Mushroom Nanosuspension and Extract Both with 5% (w/w) Concentration FIG. 17 shows the comparison of the cytokine IL-10, as one of the major pro-inflammatory cytokines, in an in-vitro induction caused by *agaricus subrufescens* nanosuspension (as prepared in Example 3.1) and extract (as prepared in Example 3.4). The induction of IL-10 by *agaricus subrufescens* nanosuspension is by a factor of 26.5 higher compared to the extract.

Example 11

Figure 18:
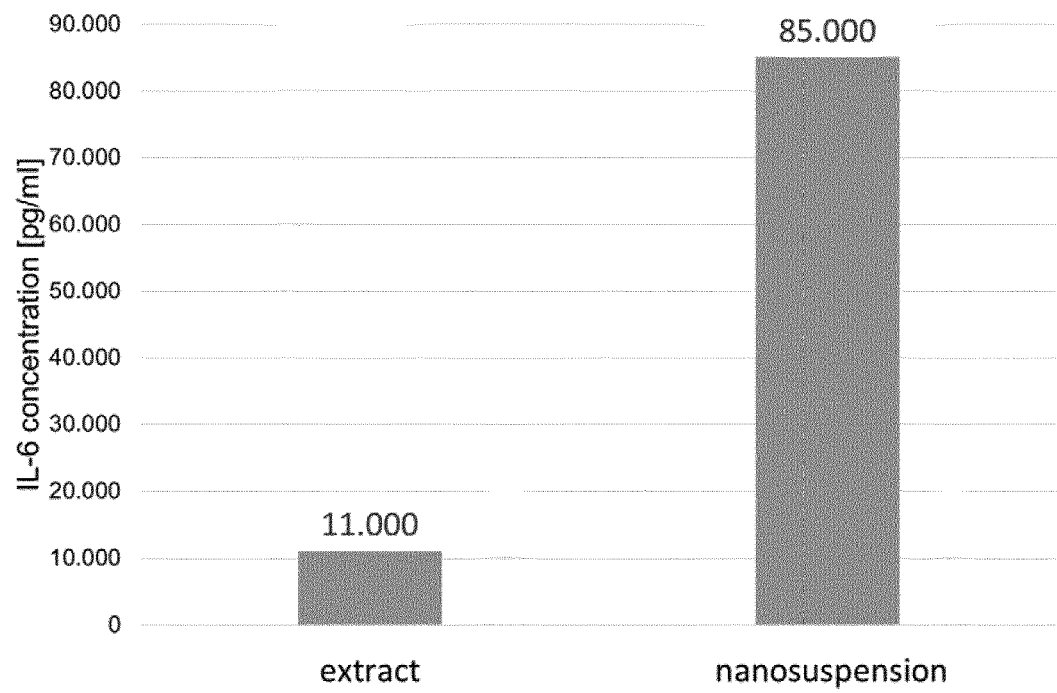
FIG. 18: shows the comparison of the cytokine IL-6 in an in-vitro induction caused by a 5% (w/w) *agaricus subrufescens* nanosuspension (as prepared in Example 3.1) and a 5% (w/w) extract (as prepared in Example 3.4).

Induction of Cytokine IL-6 by *Agaricus Subrufescens* Mushroom Nanosuspension and Extract Both with 5% (w/w) Concentration as a Resulting Effect in the Human Organism FIG. 18 shows the comparison of the cytokine IL-6, as one of the major pro-inflammatory cytokines, in an in-vitro induction caused by *agaricus subrufescens* nanosuspension (as prepared in Example 3.1) and extract (as prepared in Example 3.4). The induction of IL-10 by *agaricus subrufescens* nanosuspension is by a factor of 6.7 higher compared to the extract.

Example 12

Improvement of the Particle Distribution of an *Agaricus* Mushroom Nanosuspension with 5% (w/w) Concentration and 7.5% Lipid 150 g powder of *agaricus subrufescens* (particle size $D_{90}$: <320 µm), 225 g Lipoid P100 (7.5% (w/w)) and 15 g polysorbate Tween® 80 (0.5% (w/w)) were added to 3000 g bi-distilled water, resulting in a 5% (w/w) dispersion of *agaricus subrufescens* powder in water. The dispersion was milled in a wet ball agitator mill (type X1, Buehler AG, Switzerland) using yttrium stabilized zirconia balls of size 0.4 to 0.5 mm until the particle size ($D_{90}$) is about 15 µm, and then using yttrium stabilized zirconia balls of size 0.1 mm until the final particle size ($D_{100}$) of 375 nm is reached. At a particle size ($D_{90}$) of about 4 µm, 30 g (1% (w/w)) Kolliphor® P407 was added. The final particle size ($D_{100}$) of the nanosuspension was 375 nm. A filtration of the resulting nanosuspension was not necessary.

Figure 19:
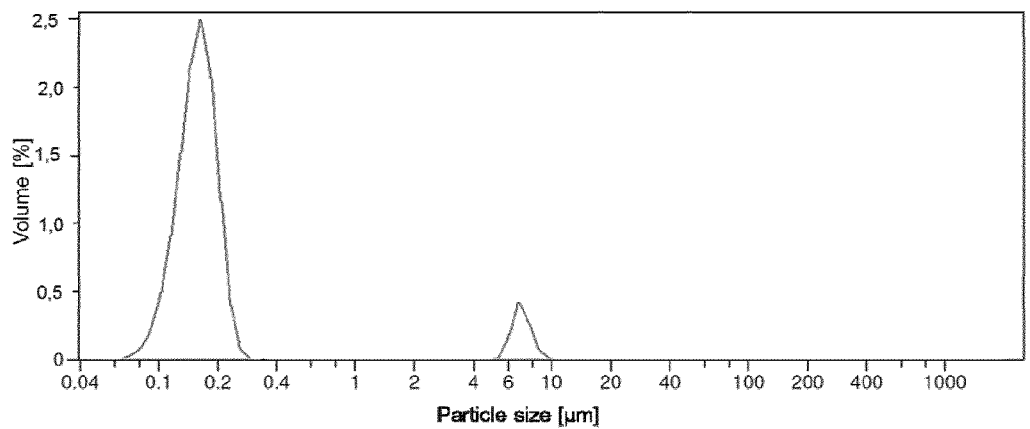
FIG. 19: shows the particle distribution by a 5% (w/w) *agaricus subrufescens* nanosuspension (as prepared in Example 3.1).
Figure 20:
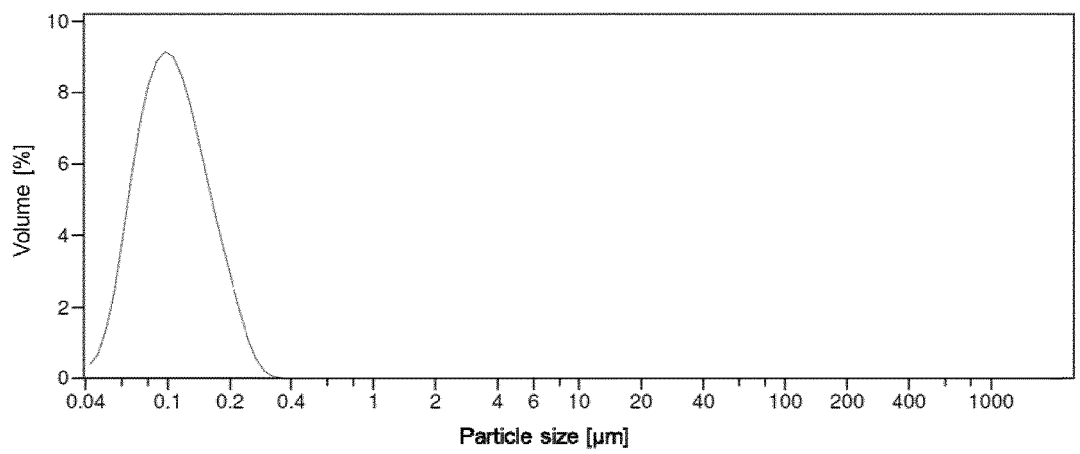
FIG. 20: shows the particle distribution by a 5% (w/w) *agaricus subrufescens* nanosuspension (as prepared in Example 12).

By the addition of further 2.5% (w/w) Lipoid P100 compared to Example 3.1, two major improvements have been achieved. At first, a final particle size ($D_{100}$) of 375 nm (see FIG. 20) as achieved, compared to a particle size ($D_{100}$) of 10 µm (see FIG. 19) in Example 3.1 Secondly, a mono-modal particle distribution resulted, compared to the bi-modal particle distribution in Example 3.1 (see FIGS. 19 and 20, respectively). To keep a nanosuspension stable, it is preferred to have a mono-modal particle distribution to avoid or reduce Ostwald ripening which may occur and result in an unstable nanosuspension. The difference is also clear from the more detailed particle distribution of the two Examples. In Example 3.1, the $D_{10}$ particle size is 0.108 µm, the $D_{50}$ particle size is 0.159 µm, the $D_{90}$ particle size is 0.240 µm, and the $D_{100}$ particle size is 10 µm (see FIG. 19). In contrast thereto, the detailed particle distribution of Example 12 is a $D_{10}$ particle size of 0.065 µm, a $D_{50}$ particle size of 0.104 µm, a $D_{90}$ particle size of 0.178 µm, and a $D_{100}$ particle size of 0.375 µm (see FIG. 20).

Example 13

Induction of CD25 Activated T-cells by *Agaricus Subrufescens* Mushroom Nanosuspension of Example 12 as a Resulting Effect in the Human Organism CD25 activated T-cells are one important T-cell subpopulation which are considered to induce a shift from T-helper cells 2 (Th2) to T-helper cells 1 (Th1) response. A shift in the Th1/Th2 balance towards a Th1 response is responsible for an increase of the virus defense capacity of the immune system. In the following Example, the increase in CD25 activated T-cells was tested in human beings with a nanosuspension according to Example 12 containing *agaricus subrufescens*, compared to a powder of *agaricus subrufescens* as available on the marked.

Figure 21:
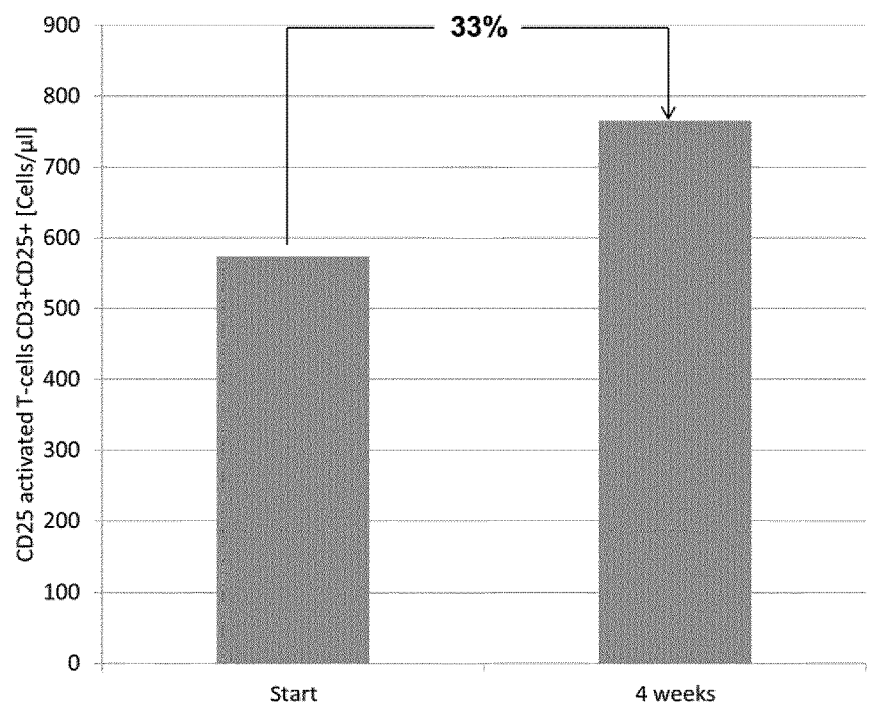
FIG. 21: shows the CD25 activated T-cells CD3+CD25+ in-vivo induction caused by a 5% (w/w) *agaricus subrufescens* nanosuspension (as prepared in Example 12) taking
Figure 22:
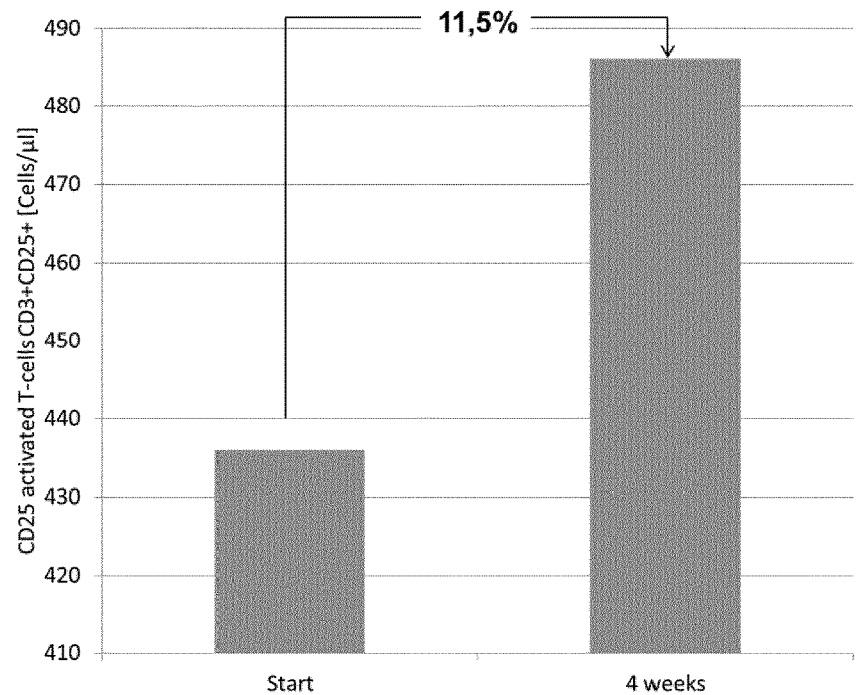
FIG. 22: shows the CD25 activated T-cells CD3+CD25+ in-vivo induction caused by an *agaricus subrufescens* powder in capsules taking.

The nanosuspension as prepared in Example 12 was mixed with propane-1,2,3-triol (glycerin) to result in a mixture containing 40% glycerin. This mixture was administered to a first group of eight human beings at a dose of 3.78 ml/day by a pump spray actuator. This dose corresponds to 105 mg *agaricus subrufescens* (dry solid content). In said first group, the CD25 activated T-cells increased by 33% within 4 weeks after start (see FIG. 21). For comparative reasons, a second group of eight human beings received *agaricus subrufescens* powder in capsules (particle size of about 220 µm) at the daily recommended dose of 2520 mg. In said second group, the CD25 activated T-cells increased by 11.5% within 4 weeks after start (see FIG. 22).

As can be seen from the above data, the nanosuspension of Example 12 results in an about threefold increase of CD25 activated T-cells, compared to a powder. In other words, the nanosuspension of Example 12 is about three times more potent than the conventional powder. This is even more surprising as the dose was lower by a factor of 24, compared to the powder.

The invention claimed is:

1. A method for the preparation of a nanosuspension, the method comprising:
    dispersing at least one natural material having a particle size ($D_{100}$) of less than 320 µm in a solvent, thereby obtaining a dispersion; and
    milling the dispersion to a particle size ($D_{90}$) of below 500 nm, wherein the nanosuspension comprises the at least one natural material, wherein the at least one natural material is at least one selected from the group consisting of plants, cyanobacteria, algae and fungi, and wherein the at least one natural material is not an extract.

2. The method according to claim 1, wherein the natural material does not comprise ginseng and/or cellulose fiber.

3. The method according to claim 1, wherein the at least one natural material is a part or the whole of a plant, a cyanobacterium, an alga, and/or a fungus.

4. The method according to claim 1, further comprising drying the natural material prior to the dispersing.

5. The method according to claim 1, wherein the solvent is water or a mixture of water and ethanol.

6. The method according to claim 1, wherein the nanosuspension is an aqueous nanosuspension or a nanosuspension on the basis of a mixture of water and ethanol.

7. The method according to claim 1, wherein the at least one natural material is dispersed in the dispersing in a concentration of from 0.5 to 20% (w/w), based on the total amount of solvent used in the nanosuspension.

8. The method according to claim 1, wherein the dispersing or the milling comprises adding a stabilizer.

9. The method according to claim 8, wherein the dispersing comprises adding a polysorbate in an amount of from 0.5 to 2% (w/w), and/or wherein the stabilizer is selected from the group consisting of polysorbate 80 and polysorbate 20.

10. The method according to claim 8, wherein the dispersing comprises adding a phospholipid in an amount of from 50 to 200% (w/w), based on the total amount of the natural material.

11. The method according to claim 1, wherein the milling is in a wet hall agitator mill.

12. The method according to claim 1, wherein the milling comprises adding a stabilizer at a particle size $D_{90}$<9 µm.

13. The method according to claim 8, wherein the stabilizer is selected from the group consisting of phospholipids; polysorbates; polymers; nonionic tri-block copolymers; copolyvinylpyrrolidone; caprylocaproyl polyoxyl-8 glycerides NF; lauroyl polyoxyl-32 glycerides NF; gelatin; lecithin (phosphatides); gum acacia; cholesterol; tragacanth; polyoxyethylene alkyl ethers; polyoxyethylene castor oil derivatives; polyoxyethylene sorbitan fatty acid esters; sorbitan fatty acid esters; polyethylene glycols; polyoxyethylene stearates; mono and diglycerides; colloidal silicon dioxide; sodium dodecylsulfate; magnesium aluminum silicate; triethanolamine; stearic acid; calcium stearate; glycerol monostearate; cetostearyl alcohol; cetomacrogol emulsifying wax; short and medium chain alcohols; oleoyl polyoxyl-6 glycerides NF; polyglycerol oleate; propane-1,2,3-triol; polyvinyl alcohol and dioctyl sodium sulfosuccinate (DOSS).

14. The method according to claim 1, wherein the method comprises adding propane-1,2,3-triol (glycerin) after the milling is finished.

15. The method according to claim 1, further comprising filtering the nanosuspension after the milling.

16. The method according to claim 1, further comprising increasing the concentration of the nanosuspension by evaporation of solvent to a concentration of the natural material of 10 to 40% (w/w), based on the total volume of the nanosuspension.

17. The method according to claim 1, wherein the at least one natural material is at least one selected from the group consisting of a cyanobacterium, an alga, a fungus, a root, a stem, a leaf, a fruit, and a flower.

18. The method according to claim 17, wherein the at least one natural material is in the form of a natural composition, wherein the at least one natural material comprises a water-soluble compound, and wherein the at least one natural material further comprises a water-insoluble compound.

19. The method according to claim 1, wherein either the nanosuspension is not filtered after milling, or after milling, the nanosuspension having a particle size $D_{90}$ of less than 500 nm obtained by the milling is filtered, thereby producing a nanosuspension with a lower particle size $D_{90}$.

20. The method according to claim 1, wherein the at least one natural material is an entire physiological part of a plant, cyanobacterium, alga, and/or fungus, or the at least one natural material is the whole of a plant, cyanobacterium, alga, and/or fungus.

* * * * *